(12) United States Patent
El Dorry et al.

(10) Patent No.: US 9,963,688 B2
(45) Date of Patent: May 8, 2018

(54) HEAVY METAL RESISTANT ESTERASE

(71) Applicants: AMERICAN UNIVERSITY OF CAIRO, New Cairo (EG); KING ABDULLAH UNIVERSITY OF SCIENCE AND TECHNOLOGY, Thuwal (SA); Hamza El Dorry, New Cairo (EG)

(72) Inventors: Hamza El Dorry, New Cairo (EG); Rania Siam, New Cairo (EG); Yasmine M. Mohamed, New Cairo (EG)

(73) Assignees: AMERICAN UNIVERSITY IN CAIRO, New Cairo (EG); King Abdullah University of Science and Technology, Thuwal (SA)

( * ) Notice: Subject to any disclaimer, the term of this patent is extended or adjusted under 35 U.S.C. 154(b) by 0 days. days.

(21) Appl. No.: 14/779,293

(22) PCT Filed: Mar. 24, 2014

(86) PCT No.: PCT/IB2014/001218
§ 371 (c)(1),
(2) Date: Sep. 22, 2015

(87) PCT Pub. No.: WO2014/147486
PCT Pub. Date: Sep. 25, 2014

(65) Prior Publication Data
US 2016/0053239 A1    Feb. 25, 2016

Related U.S. Application Data

(60) Provisional application No. 61/804,434, filed on Mar. 22, 2013.

(51) Int. Cl.
| | |
|---|---|
| *C12N 9/16* | (2006.01) |
| *C12N 11/14* | (2006.01) |
| *C12P 7/02* | (2006.01) |
| *C12P 7/40* | (2006.01) |
| *C12N 9/18* | (2006.01) |
| *C12Q 1/44* | (2006.01) |
| *A61K 38/46* | (2006.01) |
| *C11D 3/386* | (2006.01) |
| *A23L 33/18* | (2016.01) |

(52) U.S. Cl.
CPC ............... *C12N 9/18* (2013.01); *A23L 33/18* (2016.08); *A61K 38/465* (2013.01); *C11D 3/38636* (2013.01); *C12Q 1/44* (2013.01); *A23V 2002/00* (2013.01); *C12Y 301/01* (2013.01)

(58) Field of Classification Search
None
See application file for complete search history.

(56) References Cited

U.S. PATENT DOCUMENTS

| | | |
|---|---|---|
| 6,551,795 B1 | 4/2003 | Rubenfield et al. |
| 2003/0028005 A1 | 2/2003 | Bazan |
| 2009/0258406 A1 | 10/2009 | Michels et al. |
| 2011/0247985 A1 | 10/2011 | Theodore |
| 2011/0294173 A1 | 12/2011 | Holmback et al. |

FOREIGN PATENT DOCUMENTS

WO    WO 2008036061 A2 *   3/2008   ............... A62D 3/02

OTHER PUBLICATIONS

Sigma Chemical 1997 Catalog, p. 1089.*
Colman, Res Immun 145:33-36, 1996.*
Abaza et al., J Prot Chem 11:433-444, 1992.*
Mohamed et al., Sci. Rep. 3:3358, Nov. 2013, 8 pages.*
Wang et al., ISME J. 5:1652-1659, 2011.*
International Search Report dated Dec. 4, 2014 in PCT/IB14/001218 Filed Mar. 24, 2014.

* cited by examiner

*Primary Examiner* — David Steadman
(74) *Attorney, Agent, or Firm* — Oblon, McClelland, Maier & Neustadt, L.L.P.

(57) ABSTRACT

EstATII is an esterase that a halotolerant, thermophilic and resistant to a spectrum of heavy metals including toxic concentration of metals. It was isolated from the lowest convective layer of the Atlantis II Red Sea brine pool. The Atlantis II brine pool is an extreme environment that possesses multiple harsh conditions such as; high temperature, salinity, pH and high concentration of metals, including toxic heavy metals. A fosmid metagenomic library using DNA isolated from the lowest convective layer this pool was used to identify EstATII. Polynucleotides encoding EstATII and similar esterases are disclosed and can be used to make EstATII. EstATII or compositions or apparatuses that contain it may be used in various processes employing lipases/esterases especially when these processes are performed under harsh conditions that inactivate other kinds of lipases or esterases.

22 Claims, 4 Drawing Sheets

Figure 1: Atlantis II Brine Pool Sample Site
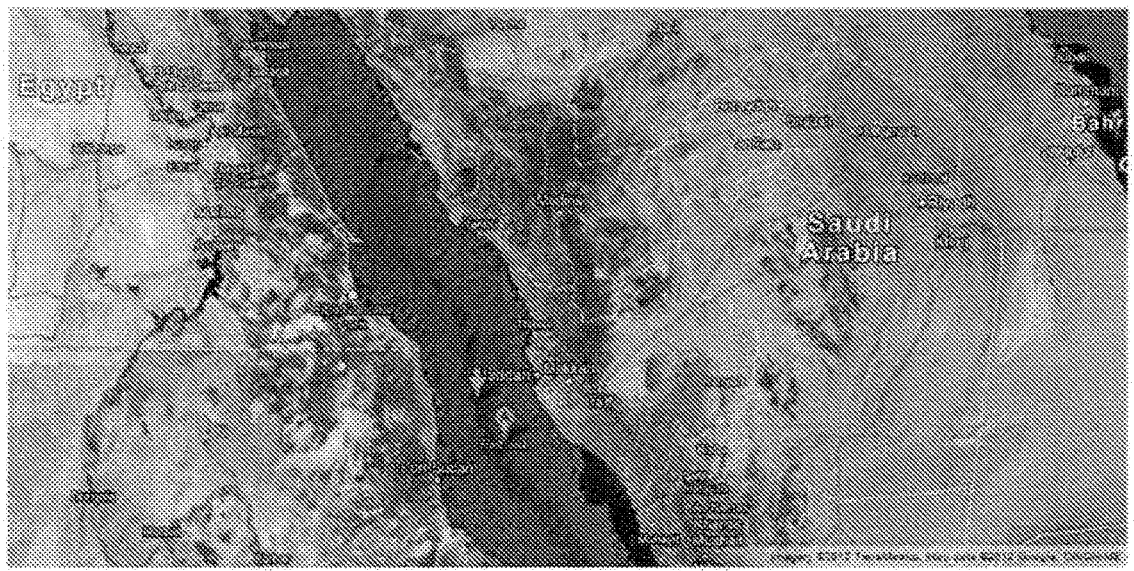
Location of the Atlantis II Brine Pool(Latitude (N) 21° and Longitude (E) 38°) from which the samples were obtained during the KAUST Red Sea 2010 expedition.

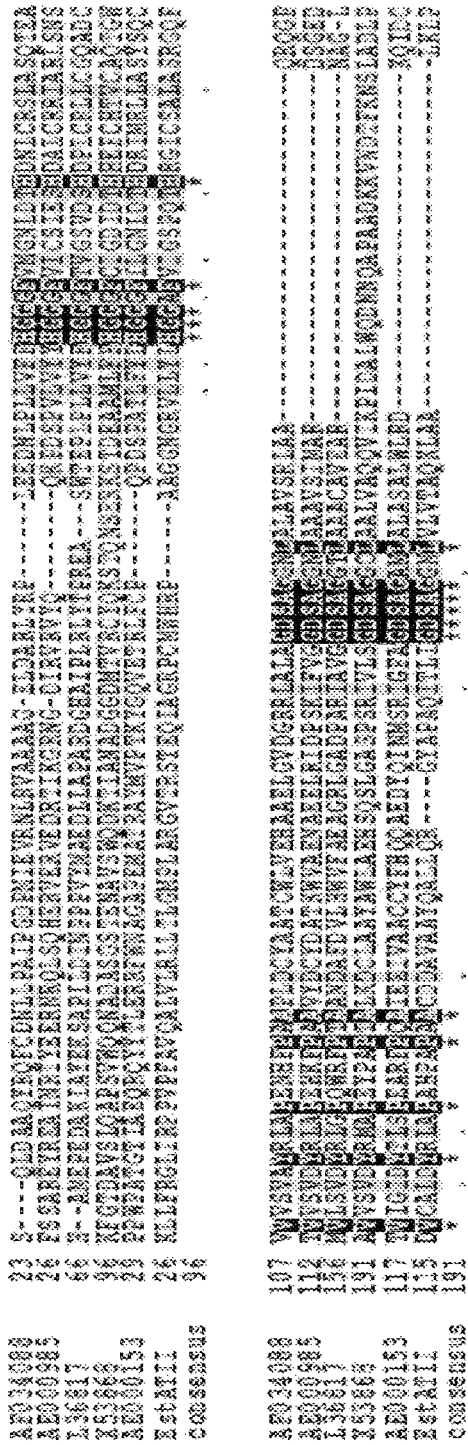
Figure 2: Conserved Motifs found in members of The Hormone Sensitive Lipase (HSL) Family and in Est-ATII

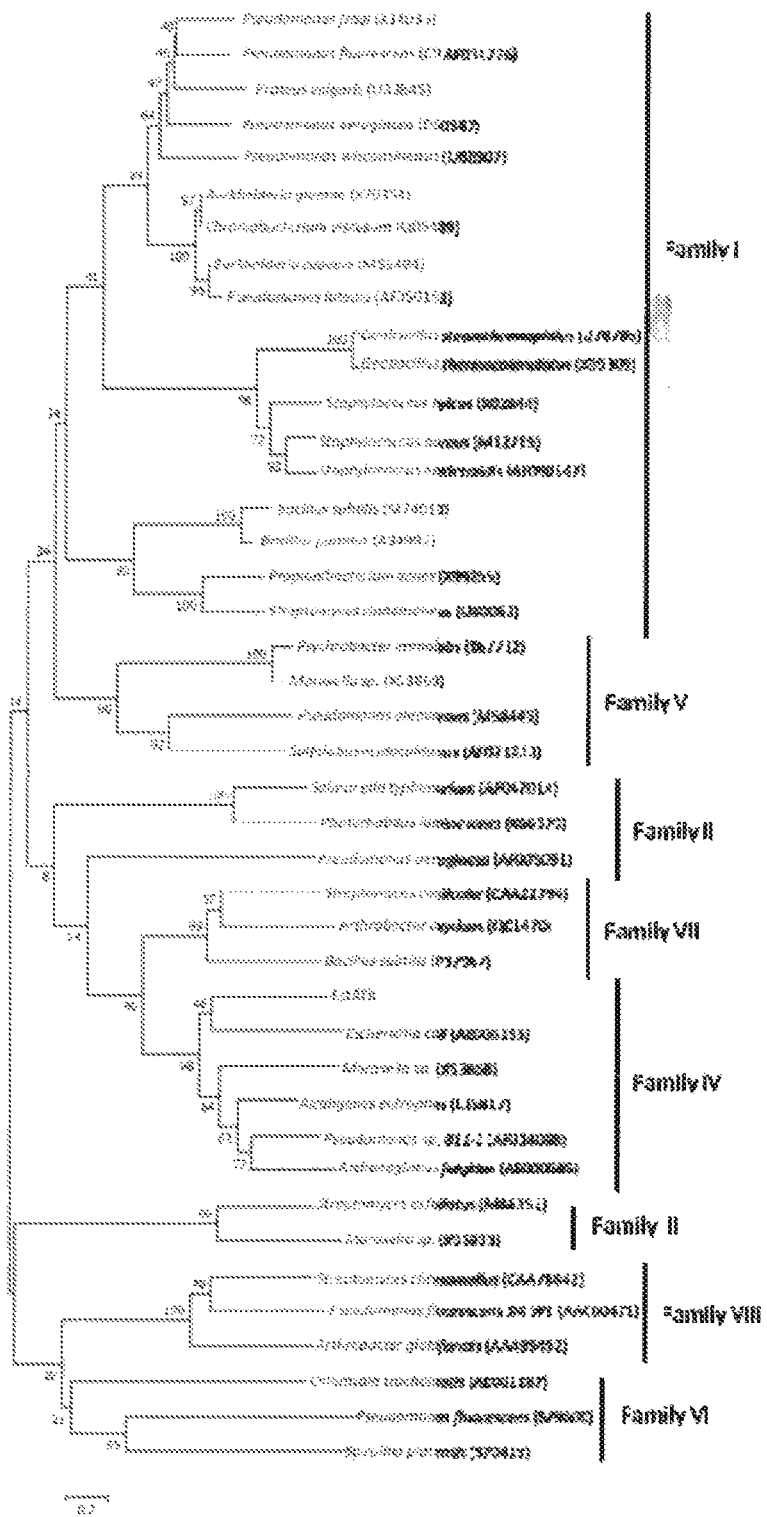
FIGURE 3: Phylogenetic Analysis and Classification of EstATII

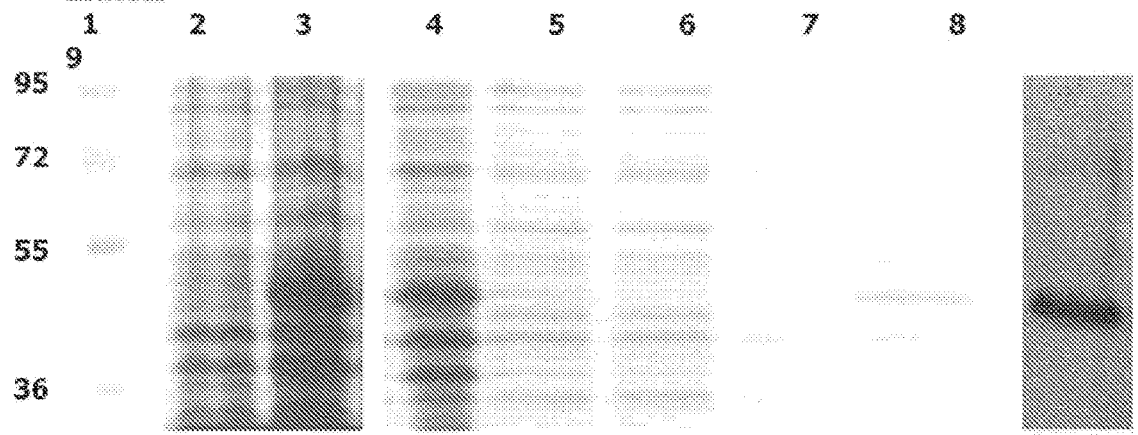
Figure 4: Overexpression, purification and western blot analysis of recombinant EstATII
Lane 1: Molecular Weight marker, Lane 2: Un-induced sample, Lane 3: Sample induced with 0.5 mM IPTG, Lane 4: Protein Lysate, Lanes 5,6: Flowthrough. Lane 7: Wash step. Lane 8: Purified EstATII. Lane 9: Western Blot analysis of purified EstATII.

SEQUENCE LISTING

```
<160> NUMBER OF SEQ ID NOS: 13

<210> SEQ ID NO 1
<211> LENGTH: 945
<212> TYPE: DNA
<213> ORGANISM: Unknown
<220> FEATURE:
<223> OTHER INFORMATION: Isolate from Atlantis II Red Sea Brine Pool
<220> FEATURE:
<221> NAME/KEY: CDS
<222> LOCATION: (1)..(945)

<400> SEQUENCE: 1 atg tcc agg tac gtt gat gag ctg tat cgc aac ccg ggc caa ccc ggc      48
Met Ser Arg Tyr Val Asp Glu Leu Tyr Arg Asn Pro Gly Gln Pro Gly
1               5                   10                  15 ctg cgc gcc ctg cgc ggc atg ctg aaa ctg ctg ttc cgg ggt ttg          96
Leu Arg Ala Leu Arg Gly Met Leu Lys Leu Leu Phe Arg Gly Leu
            20                  25                  30 atc cgt ccg ccc gtg ccc ttt gcc gtg cag gca ctg gtg ctg cgc ctg     144
Ile Arg Pro Pro Val Pro Phe Ala Val Gln Ala Leu Val Leu Arg Leu
        35                  40                  45 ctg acc ctc ggc atg ccg ctg gcc aga ggc gtg acc cgc agc acc gag     192
Leu Thr Leu Gly Met Pro Leu Ala Arg Gly Val Thr Arg Ser Thr Glu
    50                  55                  60 cag atc gcc gga cgg ccc tgt atg tgg cac cgc ccg gcc gct ggc ggc     240
Gln Ile Ala Gly Arg Pro Cys Met Trp His Arg Pro Ala Ala Gly Gly
65                  70                  75                  80 aac ggc cgc gtg ctg ctg tac ctg cat ggc ggc gcc ttc gtc atc ggc     288
Asn Gly Arg Val Leu Leu Tyr Leu His Gly Gly Ala Phe Val Ile Gly
                85                  90                  95 tcc ccg cag acc cac cgc ggc atc tgc tcg gcg ctc gcc agc cgt ggt     336
Ser Pro Gln Thr His Arg Gly Ile Cys Ser Ala Leu Ala Ser Arg Gly
            100                 105                 110 cag ttt gat gtc tgc gca ctc gat tac cga ctg gcg ccg gcg cac ccg     384
Gln Phe Asp Val Cys Ala Leu Asp Tyr Arg Leu Ala Pro Ala His Pro
        115                 120                 125 gca ccg gcg gcc tgt gac gat gcg gtc gcc gcc tat cag gcc ctg ctg     432
Ala Pro Ala Ala Cys Asp Asp Ala Val Ala Ala Tyr Gln Ala Leu Leu
    130                 135                 140 cag cga ggc tat gcg ccc gcg cag atc acc ctg atc ggc gat tcg gcg     480
Gln Arg Gly Tyr Ala Pro Ala Gln Ile Thr Leu Ile Gly Asp Ser Ala
145                 150                 155                 160 ggc ggc aac ctg gta ctg gtg acc gcg cag aaa ctg gcc gcg ctc aag     528
Gly Gly Asn Leu Val Leu Val Thr Ala Gln Lys Leu Ala Ala Leu Lys
                165                 170                 175 ctg ccg ctg ccg gcc tcg ctg gtc tgc ttt tca ccg gtc acc gac atg     576
Leu Pro Leu Pro Ala Ser Leu Val Cys Phe Ser Pro Val Thr Asp Met
            180                 185                 190 acc gcc gaa cag ctg cac gcg cct gcg gcc ggc gat cca ctg ctg cat     624
Thr Ala Glu Gln Leu His Ala Pro Ala Ala Gly Asp Pro Leu Leu His
        195                 200                 205 ccg tcc tgg cta gac agc gct cgc gac gcc tac tgc ccg gcc ggg ctg     672
Pro Ser Trp Leu Asp Ser Ala Arg Asp Ala Tyr Cys Pro Ala Gly Leu
```

```
                        210                 215                 220
gac cgc gcc gac ccg atg gtg tcg ccg ctg ttc ggc cag ctc aag ggc       720
Asp Arg Ala Asp Pro Met Val Ser Pro Leu Phe Gly Gln Leu Lys Gly
225                 230                 235                 240 ctg ccg cca ttg ctg ctg cag gtc ggt gaa gac gag gtg ctg ctg aac       768
Leu Pro Pro Leu Leu Leu Gln Val Gly Glu Asp Glu Val Leu Leu Asn
                245                 250                 255 gac agc ctg cgg ctg gcc gaa gcc gcg cgc gca gcc gac gtt gcc gta       816
Asp Ser Leu Arg Leu Ala Glu Ala Ala Arg Ala Ala Asp Val Ala Val
            260                 265                 270 cgg ctg gag cgc tac gaa gac ctg tgg cat gta ttt cag gcc cat gcc       864
Arg Leu Glu Arg Tyr Glu Asp Leu Trp His Val Phe Gln Ala His Ala
        275                 280                 285 ggg ctg ctg cac agc gcc gat gcg gcg ctg cag cgg gtg gtg gac ttt       912
Gly Leu Leu His Ser Ala Asp Ala Ala Leu Gln Arg Val Val Asp Phe
    290                 295                 300 gtg aac agc gct cag acc gac tcg gta agc tga                           945
Val Asn Ser Ala Gln Thr Asp Ser Val Ser
305                 310

<210> SEQ ID NO 2
<211> LENGTH: 314
<212> TYPE: PRT
<213> ORGANISM: Unknown
<220> FEATURE:
<223> OTHER INFORMATION: Synthetic Construct

<400> SEQUENCE: 2

Met Ser Arg Tyr Val Asp Glu Leu Tyr Arg Asn Pro Gly Gln Pro Gly
1               5                   10                  15

Leu Arg Ala Leu Leu Arg Gly Met Leu Lys Leu Leu Phe Arg Gly Leu
            20                  25                  30

Ile Arg Pro Pro Val Pro Phe Ala Val Gln Ala Leu Val Leu Arg Leu
        35                  40                  45

Leu Thr Leu Gly Met Pro Leu Ala Arg Gly Val Thr Arg Ser Thr Glu
    50                  55                  60

Gln Ile Ala Gly Arg Pro Cys Met Trp His Arg Pro Ala Ala Gly Gly
65                  70                  75                  80

Asn Gly Arg Val Leu Leu Tyr Leu His Gly Ala Phe Val Ile Gly
                85                  90                  95

Ser Pro Gln Thr His Arg Gly Ile Cys Ser Ala Leu Ala Ser Arg Gly
            100                 105                 110

Gln Phe Asp Val Cys Ala Leu Asp Tyr Arg Leu Ala Pro Ala His Pro
        115                 120                 125

Ala Pro Ala Ala Cys Asp Asp Ala Val Ala Ala Tyr Gln Ala Leu Leu
    130                 135                 140

Gln Arg Gly Tyr Ala Pro Ala Gln Ile Thr Leu Ile Gly Asp Ser Ala
145                 150                 155                 160

Gly Gly Asn Leu Val Leu Val Thr Ala Gln Lys Leu Ala Ala Leu Lys
                165                 170                 175

Leu Pro Leu Pro Ala Ser Leu Val Cys Phe Ser Pro Val Thr Asp Met
            180                 185                 190

Thr Ala Glu Gln Leu His Ala Pro Ala Gly Asp Pro Leu Leu His
        195                 200                 205

Pro Ser Trp Leu Asp Ser Ala Arg Asp Ala Tyr Cys Pro Ala Gly Leu
    210                 215                 220

Asp Arg Ala Asp Pro Met Val Ser Pro Leu Phe Gly Gln Leu Lys Gly
```

```
              225                 230                 235                 240

Leu Pro Pro Leu Leu Leu Gln Val Gly Glu Asp Val Leu Leu Asn
                245                 250                 255

Asp Ser Leu Arg Leu Ala Glu Ala Ala Arg Ala Ala Asp Val Ala Val
                260                 265                 270

Arg Leu Glu Arg Tyr Glu Asp Leu Trp His Val Phe Gln Ala His Ala
                275                 280                 285

Gly Leu Leu His Ser Ala Asp Ala Ala Leu Gln Arg Val Val Asp Phe
                290                 295                 300

Val Asn Ser Ala Gln Thr Asp Ser Val Ser
305                 310

<210> SEQ ID NO 3
<211> LENGTH: 22
<212> TYPE: DNA
<213> ORGANISM: Artificial
<220> FEATURE:
<223> OTHER INFORMATION: Synthetic Primer Est F (forward primer)

<400> SEQUENCE: 3
atgtccaggt acgttgatga gc                                             22

<210> SEQ ID NO 4
<211> LENGTH: 20
<212> TYPE: DNA
<213> ORGANISM: Artificial
<220> FEATURE:
<223> OTHER INFORMATION: Synthetic Primer  EstR (reverse primer)

<400> SEQUENCE: 4
tcagcttacc gagtcggtct                                                20

<210> SEQ ID NO 5
<211> LENGTH: 13
<212> TYPE: PRT
<213> ORGANISM: Artificial
<220> FEATURE:
<223> OTHER INFORMATION: Lipase/Esterase motif
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(12)
<223> OTHER INFORMATION: Xaa can be any naturally occurring amino acid

<400> SEQUENCE: 5

His Gly Gly Xaa Phe Xaa Xaa Xaa Xaa Xaa Xaa Xaa His
1               5                   10

<210> SEQ ID NO 6
<211> LENGTH: 12
<212> TYPE: PRT
<213> ORGANISM: Artificial
<220> FEATURE:
<223> OTHER INFORMATION: Lipase/esterase motif
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: misc_feature
<222> LOCATION: (7)..(9)
<223> OTHER INFORMATION: Xaa can be any naturally occurring amino acid
<220> FEATURE:
<221> NAME/KEY: misc_feature
```

-continued

```
<222> LOCATION: (11)..(11)
<223> OTHER INFORMATION: Xaa can be any naturally occurring amino acid

<400> SEQUENCE: 6

Val Xaa Xaa Xaa Xaa Tyr Xaa Xaa Xaa Pro Xaa Ala
1               5                   10

<210> SEQ ID NO 7
<211> LENGTH: 8
<212> TYPE: PRT
<213> ORGANISM: Artificial
<220> FEATURE:
<223> OTHER INFORMATION: Lipase/esterase motif
<220> FEATURE:
<221> NAME/KEY: misc_feature
<222> LOCATION: (6)..(7)
<223> OTHER INFORMATION: Xaa can be any naturally occurring amino acid

<400> SEQUENCE: 7

Gly Asp Ser Ala Gly Xaa Xaa Leu
1               5

<210> SEQ ID NO 8
<211> LENGTH: 5
<212> TYPE: PRT
<213> ORGANISM: Artificial
<220> FEATURE:
<223> OTHER INFORMATION: Motif

<400> SEQUENCE: 8

Gly Asp Ser Ala Gly
1               5

<210> SEQ ID NO 9
<211> LENGTH: 308
<212> TYPE: PRT
<213> ORGANISM: Pseudomonas aeruginosa
<220> FEATURE:
<221> NAME/KEY: MISC_FEATURE
<223> OTHER INFORMATION: AF034088

<400> SEQUENCE: 9

Met Pro Leu Asp Lys Gln Ile Ala Ala Val Leu Gln Gln Phe Ser Glu
1               5                   10                  15

Leu Pro Ala Pro Asp Phe Ser Gln Leu Asp Ala Ala Gln Tyr Arg Gln
            20                  25                  30

Phe Cys Asp Asn Leu Leu Pro Ala Ile Pro Gly Asp Pro Met Ile Glu
        35                  40                  45

Val Arg Asn Leu Arg Val Ala Ala Ala Gly Glu Leu Asp Ala Arg
    50                  55                  60

Leu Tyr Arg Pro Leu Glu Glu Asp Asn Leu Pro Leu Leu Val Phe Phe
65                  70                  75                  80

His Gly Gly Gly Phe Val Met Gly Asn Leu Asp Thr His Asp Asn Leu
                85                  90                  95

Cys Arg Ser Leu Ala Ser Gln Thr Glu Ala Val Val Ser Val Ala
            100                 105                 110

Tyr Arg Leu Ala Pro Glu Asn His Phe Pro Ala Ala Pro Leu Asp Cys
        115                 120                 125

Tyr Ala Ala Thr Cys Trp Leu Val Glu His Ala Ala Glu Leu Gly Val
    130                 135                 140

Asp Gly Arg Arg Leu Ala Leu Ala Gly Asp Ser Ala Gly Gly Asn Leu
145                 150                 155                 160
```

-continued

```
Ala Leu Ala Val Ser Arg Leu Ala Gln Arg Gln Gly Pro Lys Ile
            165                 170                 175

Ser Tyr Gln Cys Leu Phe Tyr Pro Val Thr Asp Ala Arg Cys Asp Ser
            180                 185                 190

Gln Ser Tyr Glu Glu Phe Ala Glu Gly Tyr Phe Leu Thr Gly Ala Met
            195                 200                 205

Met Tyr Trp Phe Trp Gln Gln Tyr Leu Gln Asp Thr Gly Gln Gly Asp
210                 215                 220

Asp Pro Leu Ala Ser Pro Leu Arg Ala Glu Thr Leu Ala Asp Leu Pro
225                 230                 235                 240

Pro Thr Thr Leu Ile Thr Ala Glu Phe Asp Pro Leu Arg Asp Glu Gly
            245                 250                 255

Glu Ala Phe Ala Leu Arg Leu Gln Gln Ala Gly Val Ser Val Arg Val
            260                 265                 270

Gln Arg Cys Glu Gly Met Ile His Gly Phe Ile Ser Met Ala Pro Phe
            275                 280                 285

Val Glu Arg Ala Ala His Ala Leu Ser Asp Ala Ala Asp Leu Arg
            290                 295                 300

Arg Ala Leu Asn
305

<210> SEQ ID NO 10
<211> LENGTH: 311
<212> TYPE: PRT
<213> ORGANISM: Archaeoglobus fulgidus
<220> FEATURE:
<221> NAME/KEY: MISC_FEATURE
<223> OTHER INFORMATION: AE00985

<400> SEQUENCE: 10

Met Leu Asp Met Pro Ile Asp Pro Val Tyr Tyr Gln Leu Ala Glu Tyr
1               5                   10                  15

Phe Asp Ser Leu Pro Lys Phe Asp Gln Phe Ser Ser Ala Arg Glu Tyr
            20                  25                  30

Arg Glu Ala Ile Asn Arg Ile Tyr Glu Glu Arg Asn Arg Gln Leu Ser
        35                  40                  45

Gln His Glu Arg Val Glu Arg Val Glu Asp Arg Thr Ile Lys Gly Arg
    50                  55                  60

Asn Gly Asp Ile Arg Val Arg Val Tyr Gln Gln Lys Pro Asp Ser Pro
65                  70                  75                  80

Val Leu Val Tyr Tyr His Gly Gly Gly Phe Val Ile Cys Ser Ile Glu
                85                  90                  95

Ser His Asp Ala Leu Cys Arg Arg Ile Ala Arg Leu Ser Asn Ser Thr
            100                 105                 110

Val Val Ser Val Asp Tyr Arg Leu Ala Pro Glu His Lys Phe Pro Ala
        115                 120                 125

Ala Val Tyr Asp Cys Tyr Asp Ala Thr Lys Trp Val Ala Glu Asn Ala
    130                 135                 140

Glu Glu Leu Arg Ile Asp Pro Ser Lys Ile Phe Val Gly Gly Asp Ser
145                 150                 155                 160

Ala Gly Gly Asn Leu Ala Ala Val Ser Ile Met Ala Arg Asp Ser
                165                 170                 175

Gly Glu Asp Phe Ile Lys His Gln Ile Leu Ile Tyr Pro Val Val Asn
            180                 185                 190

Phe Val Ala Pro Thr Pro Ser Leu Leu Glu Phe Gly Glu Gly Leu Trp
        195                 200                 205
```

```
Ile Leu Asp Gln Lys Ile Met Ser Trp Phe Ser Gln Tyr Phe Ser
        210                 215                 220

Arg Glu Glu Asp Lys Phe Asn Pro Leu Ala Ser Val Ile Phe Ala Asp
225                 230                 235                 240

Leu Glu Asn Leu Pro Pro Ala Leu Ile Ile Thr Ala Glu Tyr Asp Pro
                245                 250                 255

Leu Arg Asp Glu Gly Glu Val Phe Gly Gln Met Leu Arg Arg Ala Gly
                260                 265                 270

Val Glu Ala Ser Ile Val Arg Tyr Arg Gly Val Leu His Gly Phe Ile
        275                 280                 285

Asn Tyr Tyr Pro Val Leu Lys Ala Ala Arg Asp Ala Ile Asn Gln Ile
        290                 295                 300

Ala Ala Leu Leu Val Phe Asp
305                 310

<210> SEQ ID NO 11
<211> LENGTH: 327
<212> TYPE: PRT
<213> ORGANISM: Alcaligenes eutrophus
<220> FEATURE:
<221> NAME/KEY: MISC_FEATURE
<223> OTHER INFORMATION: L36817

<400> SEQUENCE: 11

Met Gln Arg Arg His Phe Ile Ala Arg Ala Gly Ile Ala Ala Ala Thr
1               5                   10                  15

Ala Ala Leu Gly Leu Ala Ala Met Pro Ala Gln Ala Gln Ala Asp Lys
                20                  25                  30

Phe Pro Gln Arg Pro Ile Arg Leu Val Ile Gly Tyr Thr Ala Gly Gly
            35                  40                  45

Ser Thr Asp Ile Pro Phe Arg Val Leu Ala Asp Asn Ala Ser Lys Ile
        50                  55                  60

Leu Gly Gln Pro Val Ile Val Glu Asn Lys Pro Gly Ala Gly Gly Val
65                  70                  75                  80

Leu Pro Ala Gln Met Met Gln Ser Thr Ala Pro Asp Gly Tyr Thr Leu
                85                  90                  95

Ala Gln Val Ala Met Pro Val Tyr Arg Leu Pro Tyr Thr Thr Lys Ile
                100                 105                 110

Asn Trp Asp Pro Val Lys Asp Leu Asn Tyr Ile Ile Asn Leu Ala Gly
            115                 120                 125

Tyr Ser Phe Gly Leu Val Val Pro Ala Asp Ser Pro Ile Lys Thr Met
        130                 135                 140

Gln Glu Tyr Ile Ala Tyr Ala Lys Ala Asn Pro Gly Lys Leu Thr Tyr
145                 150                 155                 160

Gly Ser Pro Gly Ser Met Thr Thr Leu His Leu Thr Met Glu Glu Leu
                165                 170                 175

Ala Met Lys Gln Gly Val Gln Phe Ser His Ile Pro Tyr Lys Gly Asn
                180                 185                 190

Ser Glu Ser Met Gln Ala Leu Leu Gly Gly His Val Met Ser Val Ala
            195                 200                 205

Asp Thr Pro Ala Trp Ala Pro Tyr Val Glu Gln Gly Lys Leu Arg Leu
        210                 215                 220

Leu Ser Thr Trp Gly Glu Lys Arg Ser Ala Arg Phe Pro Ser Val Pro
225                 230                 235                 240

Thr Leu Lys Glu Leu Gly Ile Gly Ile Val Gln Thr Ser Pro Phe Gly
```

```
                        245                 250                 255
Leu Val Ala Pro Lys Gly Thr Asp Pro Lys Ile Val Gln Lys Leu His
            260                 265                 270

Asp Ala Phe Lys Lys Ala Met Asp Met Pro Asn Tyr Arg Glu Ser Leu
        275                 280                 285

Ala Lys Phe Asp Met Glu Pro Tyr Tyr Met Asn Ser Gln Gln Tyr Ala
    290                 295                 300

Gln Phe Ala Ala Glu Thr Val Lys Lys Glu Lys Ala Ile Ile Glu Lys
305                 310                 315                 320

Leu Gly Leu Ala Lys Ala Gln
                325

<210> SEQ ID NO 12
<211> LENGTH: 433
<212> TYPE: PRT
<213> ORGANISM: Moraxella sp.
<220> FEATURE:
<221> NAME/KEY: MISC_FEATURE
<223> OTHER INFORMATION: X53868

<400> SEQUENCE: 12

Met Pro Ile Leu Pro Val Pro Ala Leu Asn Ala Leu Leu Thr Lys Thr
1               5                   10                  15

Ile Lys Thr Ile Lys Thr Gly Ala Ala Lys Asn Ala His Gln His His
            20                  25                  30

Val Leu His His Thr Leu Lys Gly Leu Asp Asn Leu Pro Ala Pro Val
        35                  40                  45

Leu Glu Arg Ile Asn Arg Arg Leu Lys Ala Ser Thr Ala Glu Gln Tyr
    50                  55                  60

Pro Leu Ala Asp Ala His Leu Arg Leu Ile Leu Ala Ile Ser Asn Lys
65                  70                  75                  80

Leu Lys Arg Pro Leu Ala Ile Asp Lys Leu Pro Lys Leu Arg Gln Lys
            85                  90                  95

Phe Gly Thr Asp Ala Val Ser Leu Gln Ala Pro Ser Val Trp Gln Gln
        100                 105                 110

Asn Ala Asp Ala Ser Gly Ser Thr Glu Asn Ala Val Ser Trp Gln Asp
    115                 120                 125

Lys Thr Ile Ala Asn Ala Asp Gly Gly Asp Met Thr Val Arg Cys Tyr
130                 135                 140

Gln Lys Ser Thr Gln Asn Ser Glu Arg Lys Ser Thr Asp Glu Ala Ala
            150                 155                 160
145

Met Leu Phe Phe His Gly Gly Phe Cys Ile Gly Asp Ile Asp Thr
        165                 170                 175

His His Glu Phe Cys His Thr Val Cys Ala Gln Thr Gly Trp Ala Val
    180                 185                 190

Val Ser Val Asp Tyr Arg Met Ala Pro Glu Tyr Pro Ala Pro Thr Ala
        195                 200                 205

Leu Lys Asp Cys Leu Ala Ala Tyr Ala Trp Leu Ala Glu His Ser Gln
    210                 215                 220

Ser Leu Gly Ala Ser Pro Ser Arg Ile Val Leu Ser Gly Asp Ser Ala
225                 230                 235                 240

Gly Gly Cys Leu Ala Ala Leu Val Ala Gln Gln Val Ile Lys Pro Ile
            245                 250                 255

Asp Ala Leu Trp Gln Asp Asn Asn Gln Ala Pro Ala Ala Asp Lys Lys
        260                 265                 270
```

```
Val Asn Asp Thr Phe Lys Asn Ser Leu Ala Asp Leu Pro Arg Pro Leu
            275                 280                 285

Ala Gln Leu Pro Leu Tyr Pro Val Thr Asp Tyr Glu Ala Glu Tyr Pro
        290                 295                 300

Ser Trp Glu Leu Tyr Gly Glu Gly Leu Leu Asp His Asn Asp Ala
305                 310                 315                 320

Glu Val Phe Asn Ser Ala Tyr Thr Gln His Ser Gly Leu Pro Gln Ser
                325                 330                 335

His Pro Leu Ile Ser Val Met His Gly Asp Asn Thr Gln Leu Cys Pro
            340                 345                 350

Ser Tyr Ile Val Val Ala Glu Leu Asp Ile Leu Arg Asp Glu Gly Leu
        355                 360                 365

Ala Tyr Ala Glu Leu Leu Gln Lys Glu Gly Val Gln Val Gln Thr Tyr
    370                 375                 380

Thr Val Leu Gly Ala Pro His Gly Phe Ile Asn Leu Met Ser Val His
385                 390                 395                 400

Gln Gly Leu Gly Asn Gln Thr Thr Tyr Ile Ile Asn Glu Phe Ala Cys
                405                 410                 415

Leu Val Gln Asn Leu Leu Thr Ser Glu Gly Asp Lys Pro Asn Leu Arg
            420                 425                 430

Ala

<210> SEQ ID NO 13
<211> LENGTH: 319
<212> TYPE: PRT
<213> ORGANISM: Escherichia coli
<220> FEATURE:
<221> NAME/KEY: MISC_FEATURE
<223> OTHER INFORMATION: AE00153

<400> SEQUENCE: 13

Met Lys Pro Glu Asn Lys Leu Pro Val Leu Asp Leu Ile Ser Ala Glu
1               5                   10                  15

Met Lys Thr Val Val Asn Thr Leu Gln Pro Asp Leu Pro Pro Trp Pro
            20                  25                  30

Ala Thr Gly Thr Ile Ala Glu Gln Arg Gln Tyr Tyr Thr Leu Glu Arg
        35                  40                  45

Arg Phe Trp Asn Ala Gly Ala Pro Glu Met Ala Thr Arg Ala Tyr Met
    50                  55                  60

Val Pro Thr Lys Tyr Gly Gln Val Glu Thr Arg Leu Phe Cys Pro Gln
65                  70                  75                  80

Pro Asp Ser Pro Ala Thr Leu Phe Tyr Leu His Gly Gly Gly Phe Ile
                85                  90                  95

Leu Gly Asn Leu Asp Thr His Asp Arg Ile Met Arg Leu Leu Ala Ser
            100                 105                 110

Tyr Ser Gln Cys Thr Val Ile Gly Ile Asp Tyr Thr Leu Ser Pro Glu
        115                 120                 125

Ala Arg Phe Pro Gln Ala Ile Glu Glu Ile Val Ala Ala Cys Cys Tyr
    130                 135                 140

Phe His Gln Gln Ala Glu Asp Tyr Gln Ile Asn Met Ser Arg Ile Gly
145                 150                 155                 160

Phe Ala Gly Asp Ser Ala Gly Ala Met Leu Ala Leu Ala Ser Ala Leu
                165                 170                 175

Trp Leu Arg Asp Lys Gln Ile Asp Cys Gly Lys Val Ala Gly Val Leu
            180                 185                 190
```

```
Leu Trp Tyr Gly Leu Tyr Gly Leu Arg Asp Ser Val Thr Arg Arg Leu
    195                 200                 205

Leu Gly Gly Val Trp Asp Gly Leu Thr Gln Gln Asp Leu Gln Met Tyr
    210                 215                 220

Glu Glu Ala Tyr Leu Ser Asn Asp Ala Asp Arg Glu Ser Pro Tyr Tyr
225                 230                 235                 240

Cys Leu Phe Asn Asn Asp Leu Thr Arg Glu Val Pro Pro Cys Phe Ile
            245                 250                 255

Ala Gly Ala Glu Phe Asp Pro Leu Leu Asp Asp Ser Arg Leu Leu Tyr
            260                 265                 270

Gln Thr Leu Ala Ala His Gln Gln Pro Cys Glu Phe Lys Leu Tyr Pro
        275                 280                 285

Gly Thr Leu His Ala Phe Leu His Tyr Ser Arg Met Met Lys Thr Ala
        290                 295                 300

Asp Glu Ala Leu Arg Asp Gly Ala Gln Phe Phe Thr Ala Gln Leu
305                 310                 315
```

HEAVY METAL RESISTANT ESTERASE

CROSS-REFERENCE TO RELATED APPLICATIONS

This application claims priority to U.S. provisional application 61/804,434, filed Mar. 22, 2013, the content of which is incorporated by reference in its entirety.

BACKGROUND OF THE INVENTION

Field of the Invention

A polypeptide esterase that is resistant to inactivation by heavy metals and other extreme conditions. Polynucleotides encoding this esterase.

Description of the Related Art

Until lately, and despite its uniqueness, the Red Sea has received little attention among marine environments. The Red Sea formed 3-5 million years ago when the Arabian and African plates started to split[1]. It is characterized by high temperature and salinity owing to the high rate of evaporation, lack of major river inflows and a low rate of rainfall[1]. The Red Sea is characterized by the presence of deep-sea hypersaline anoxic basins; called brine pools, which are large bodies of water at the bottom of the ocean characterized by high temperature and salinity. To date, twenty-five brine pools have been found in the Red Sea[1, 2]. Atlantis II Deep (FIG. 1) is the largest brine pool in the Red Sea, has the highest temperature and is the most dynamic[1,3]. It has a maximum depth of 2,194 m and is stratified into several layers that increase in temperature and salinity with increasing depth; the brine-seawater interface, upper convective, middle convective and lower convective layers (LCL)[1, 3]. The lowest layer; LCL is characterized by a temperature of 68.2° C., pH value of 5.3 and salinity of 270 psu, which is 7.5 times that of normal seawater[1, 3]. Atlantis II Deep is nearly anoxic and has high concentrations of iron, zinc, copper and other heavy metals[1, 3]. Together, these extreme conditions make the Atlantis II brine pool an attractive site for mining for biocatalysts, such as lipolytic enzymes, which are predicted to possess desirable traits, including and not limited to, thermo-tolerance, halo-tolerance, pH plasticity and resistance to inhibition by heavy metals.

Industrialized societies are moving towards white (industrial) biotechnology, which has proven to be environmentally sound and commercially efficient[4]. This poses a continuous demand for novel biocatalysts, preferably biocatalysts that demonstrate high activity over a wide range of conditions such as temperature, salinity, pH and metal concentration. Biocatalysts of microbial origin represent the majority of biocatalysts used in industrial and biotechnological processes[5]. This owes to the capability of prokaryotes to populate and adapt to different environments, from hydrothermal vents to Antarctic desert soil, from which a wide array of biocatalysts are derived that are robust within a flexible range of conditions; making them desirable for industry[6].

Metagenomics serves as a powerful tool to access the genomes of the unculturable majority of prokaryotes, and to investigate their potential as sources of novel biocatalysts. It has led to the identification and characterization of a vast number of biocatalysts that are active under a wide range of conditions reflecting the environment from which they originate, making them desirable for industrial use[7-10].

Microbial lipolytic enzymes possess a huge potential as industrial biocatalysts. They are characterized by substrate specificity, regio- and enantioselectivity that surpasses that of any other enzyme, making their application potential boundless[11]. Using lipolytic enzymes in industrial and biotechnological applications is estimated to be a billion dollar business[12]. Their applications include and are not limited to leather manufacture, flavor development in the dairy industry, oil biodegradation and the synthesis of pharmaceuticals and chemicals[12-15].

As of 2005, only a dozen thermostable lipases/esterases had been isolated; Rhee J-K et. Al. (2005)[45], *New thermophilic and thermostable esterase with sequence homology to the hormone sensitive lipase family, cloned from a metagenomic library*. Appl Environ Microbiol Vol. 71(2): pp. 817-825. A 2010 paper reported that, surprisingly, only 7 esterases of thermophilic origin had been sequenced. Yu, et al. (2010)[46], *Gene cloning and characterization of a novel thermophilic esterase from Fervidobacterium nodosum Rt17-B1*, Acta Biochim. Biophys. Sin., Vol. 42(4), pp. 288-295 described a new candidate termed FNE acetylesterase, isolated from *Fervidobacterium nodosum* strain Rt17-B12. Another publication, Waters D M et al (2012)[47], *Cloning, Overexpression in Escherichia coli, and Characterization of a Thermostable Fungal Acetylxylan Esterase from Talaromyces emersonii*, Appl. Environ. Microbiol. Vol. 78(10): pp. 3759-3762 recently identified thermostable esterase from *Talaromyces emersonii* bears sequence homology to acetylxylan esterases.

The global market for lipases is significant. The division of the entire market for lipases is detergent (42%), pulp and paper (about 7%), leather (about 6%), dairy products (about 17%), and sweeteners (about 21%) (otd.unc.edu/documents/11_4_2010_Williams.pptx). The biofuels market, which is expected to grow significantly in its need for novel biocatalysts, is seen as the greatest opportunity for expanding the use of esterases. Over 300 industrial processes have been designed that rely on biocatalysts (Singh R K et al (2013)[48], *From protein engineering to immobilization: promising strategies for the upgrade of industrial enzymes*. Int. J. Mol. Sci. Vol. 14: pp. 1232-1277). Esterases are of particular use in the production of bulk chemicals and pharmaceuticals, where they find very specific niches in chemical production. Examples include precursors for pyrethrin insecticides; in the production of naproxen; solubilization of certain antibiotics; and often as a general mild remover of protective groups on chemical intermediates during various syntheses (Bornscheuer UT (2002)[49] *Microbial carboxyl esterases: classification, properties, and application in biocatalysis*. FEMS Microbiol. Rev. Vol. 26: pp. 73-81). A recent paper described the use of a thermostable esterase from *Archaeoglobus fulgidus* (Cao H et al (2012)[50] *Biocatalytic synthesis of poly (δ-valerolactone) using a thermophilic esterase from Archaeoglobus fulgidus as catalyst*. Int. J. Mol. Sci. Vol. 13: pp 12232-12241) for producing polymers useful in preparing nanoparticles for targeted therapeutic delivery, as an example. Esterases that have recently received particular attention in industrial use include furoyl esterases, pectin esterases, acetylxylan esterases, and rhamnogalacturonan acetyl esterases. The first two types are commonly used in food processing, while the latter two find use in biomass solubilization. In addition to the biofuels market, enzymatic cleavage of these molecules can contribute to production of components of nutraceuticals, cosmetics, and fine chemicals.

BRIEF SUMMARY OF THE INVENTION

The inventors disclose herein the isolation and biochemical characterization of a novel esterase; EstATII from the lower convective layer of the Atlantis II brine pool. This esterase has been biochemically characterized and is active over a range of temperatures and pH's, retains activity in the presence of agents such heavy metals including copper, zinc and mercury which inactivate many other esterases. Polynucleotides encoding EstATII and enzymatically active variants of this esterase (EstATII-type esterases) as well as recombinant methods for making it are disclosed. The EstATII-type of esterase may be used to process or transform various substrates on which it is active especially under conditions that inactive other kinds of esterases.

BRIEF DESCRIPTION OF THE DRAWINGS

FIG. 1: Atlantis II Brine Pool Sample Site. Location of the Atlantis II Brine Pool(Latitude (N) 21° and Longitude (E) 38°) from which the samples were obtained during the KAUST Red Sea 2010 expedition.

FIG. 2: Conserved Motifs found in members of The Hormone Sensitive Lipase (HSL) Family and in EstATII. Multiple sequence alignment of EstATII (SEQ ID NO: 2) with other members of the HSL family: *Pseudomonas* sp. B11-1 (AF034088)(SEQ ID NO: 9), *Archaeoglobus fulgidus* (AE000985)(SEQ ID NO: 10), *Alcaligenes eutrophus* (L36817)(SEQ ID NO: 11), *Moraxella* sp. (X53868)(SEQ ID NO: 12) and *Escherichia coli* (AE000153)(SEQ ID NO: 13) was performed using ClustalWand visualized by BoxShade server. The alignment shows the conserved motif HGG, which is involved in the formation of the oxyanion hole. It also shows the nucleophilic catalytic serine residue in the pentapeptide GDSAG (SEQ ID NO: 8), which is conserved in HSL family.

FIG. 3: Phylogenetic Analysis and Classification of EstATII

Multiple sequence alignment of EstAII with 41 lipolytic enzymes (representing the eight families of the bacterial lipolytic enzymes as classified by Arpigny and Jaeger, 1999[17]) was used to construct a phylogenetic tree. EstATII groups with members of family IV also known as the HSL family. The confidence level of the tree was estimated by bootstrapping (10,000 replicates). The tree was constructed using MEGA 5 and the scale represents the number of amino acids substitution.

FIG. 4: Overexpression, purification and western blot analysis of recombinant EstATII. Lane 1: Molecular Weight marker, Lane 2: Un-induced sample, Lane 3: Sample induced with 0.5 mM IPTG, Lane 4: Protein Lysate, Lanes 5,6: Flowthrough. Lane 7: Wash step. Lane 8: Purified EstATII. Lane 9: Western Blot analysis of purified EstATII.

DETAILED DESCRIPTION OF THE INVENTION

A polynucleotide comprising or consisting of a sequence that is at least 80%, 82.5%, 85%, 87.5%, 90%, 92.5%, 95%, 97.5%, 98%, 99% or 100% identical to the polynucleotide sequence described by SEQ ID NO: 1 or a fragment thereof that encodes a polypeptide having esterase activity. Polynucleotide encoding immunogenic fragments of the polypeptide described by SEQ ID NO: 2 are also contemplated, especially those encoding immunogenic fragments containing epitopes that specifically identify or distinguish the esterase of SEQ ID NO: 2 from other esterases or lipases. Polynucleotide sequence identity to a reference sequence, such as SEQ ID NO: 1, may be determined using BLASTn using the default setting. Preferred parameters for determining polynucleotide sequence identity when using the BLASTN program (Altschul, S. et al., Journal of Molecular Biology 215 (1990), pages 403-410) are: Expect Threshold: 10; Word size: 28; Match Score: 1; Mismatch Score: −2; Gap costs: Linear.

The polynucleotide sequences of the invention also include those that hybridize under stringent conditions to the polynucleotide sequence of SEQ ID NO: 1 or its full complement where stringent conditions can comprise washing in 4×SSC and 0.1% SDS for 15 mins at 65° C., 2×SSC and 0.1% SDS for 15 mins at 65° C. 1×SSC and 0.1% SDS for 15 mins at 65° C., 0.5×SSC and 0.1% SDS for 15 mins at 65° C., or in 0.1×SSC containing 0.1% SDS for 15 mins at 68° C. The polynucleotides that hybridize under stringent conditions may be further selected to encode polypeptides having enzymatic activity, specifically esterase activity.

Polynucleotides according to the invention may be isolated from natural sources, from a library, such as a metagenomic library, or made recombinantly or synthetically using standard techniques such as isolation from a plasmid, amplification, e.g., by the polymerase chain reaction, or by chemical synthesis. Isolated polynucleotides have been removed from other components present in their natural environments or produced during their amplification or synthesis. An isolated polynucleotide may be at least 70%, 80%, 90%, 95% or substantially free of other contaminating polynucleotides or other components. Similarly an isolated polypeptide may be at least 70%, 80%, 90%, 95% or substantially free of other contaminating polypeptides or other components it is associated with prior to its isolation.

The polynucleotides described above may encode a polypeptide comprising at least one of the motifs HGGXFXXXXXXXH (SEQ ID NO: 5), VXXXXYXXX-PXXXXPXA (SEQ ID NO: 6), or GDSAGXXL (SEQ ID NO: 7). Advantageously this peptide will exhibit esterase activity even at high temperatures and pressures or in the presence of metals, detergents and chaotropic agents or comprise epitopes that permit it or its fragments to be recognized by a mammalian humoral or cellular immune system.

The polynucleotide described above may be inserted or appear in a vector or DNA construct, such as a bacterial vector (e.g., phage, plasmid or cosmid); a yeast vector; an insect cell vector; a plant cell vector; and a vector for a mammalian cell or other kind of animal cell; wherein any of said vector may optionally comprise one or more regulatory sequences to enhance or control transcription and/or translation of said polynucleotide. Vectors include both cloning and expression vectors as well as vectors that contain chimeric genes containing all or part of the polynucleotide sequences disclosed herein (e.g., those that are at least 80% identical to reference sequence of SEQ ID NO: 1) and optionally polynucleotide encoding other functional sequences, or polynucleotides that encode fusion proteins.

The polynucleotide or vector as described above may be transformed or recombined into a host cell, such as bacterium (e.g., *Escherichia coli* or *Bacillus subtilis*), including a bacterium of Family IV or the Hormone Sensitive Lipase ("HSL") family; a yeast cell, an insect cell, a mammalian cell, an avian cell, a reptilian cell, an amphibian cell, or other kinds of transformable animal, fungal, or plant cells.

The polynucleotide, vectors and host cells described herein may be employed to produce a recombinant or synthetic protein, such as a polypeptide that is at least 80% similar or identical to reference sequence of SEQ ID NO: 2. Such a method will involve expressing the polynucleotide encoding the protein under suitable conditions, such as culturing a host cell containing a vector carrying a polynucleotide encoding the polypeptide and recovering or purifying the protein from the culture medium or from the cells. Advantageously, the recovered protein will have esterase activity as described herein.

Another aspect of the invention is a polypeptide that comprises a sequence that is at least 80%, 82.5%, 85%, 87.5%, 90%, 92.5%, 95%, 97.5%, 98%, 99% or 100% similar to SEQ ID NO: 2 or that is at least 80%, 82.5%, 85%, 87.5%, 90%, 92.5%, 95%, 97.5%, 98%, 99% or 100% identical to the amino acid sequence of SEQ ID NO: 2 or an immunogenic fragment thereof or a fragment thereof having esterase activity. As mentioned above, this polypeptide may contain one of the motifs HGGXFXXXXXXXH (SEQ ID NO: 5), VXXXXYXXXPXXXXPXA (SEQ ID NO: 6), or GDSAGXXL (SEQ ID NO: 7) found in members of the Hormone Sensitive Lipase ("HSL") family. Enzymatically active fragments of the polypeptide of the invention may have the above degrees of similarity or identity to the portion of SEQ ID NO: 2 depicted in FIG. 2 and such fragments may be embedded in longer polypeptide constructs to confer enzymatic activity on the construct.

BLASTP may be used to identify an amino acid sequence having at least 80%, 82.5%, 85%, 87.5%, 90%, 92.5%, 95%, 97.5%, 98%, 99% or 100% sequence similarity or 80%, 82.5%, 85%, 87.5%, 90%, 92.5%, 95%, 97.5%, 98%, 99% or 100% sequence identity to a reference amino acid sequence using a similarity matrix. Similarity matrices include BLOSUM45, BLOSUM62 or BLOSUM80. Unless otherwise indicated a similarity score will be based on use of BLOSUM62. Specific default parameters are Expect threshold=10; word size=3; Max matches in a query range=0; Gap Cost=Existence 11, extension 1; Compositional adjustment=conditional compositional score matrix adjustment;

When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity of similarity to the amino acid sequences disclosed herein are contemplated and encompassed by this disclosure. Variant or engineered polypeptides and polypeptide enzymes of the invention may contain 1, 2, 3, 4, 5, 6, 7, 8, 9, 10, 11, 12, 13, 14, 15, 16, 17, 18, 19, 20 or more additions, insertions, substitutions, or deletions from the amino acid sequence given by SEQ ID NO: 2 and the invention also encompasses the corresponding polynucleotide sequences encoding these variants.

As used herein the term "enzyme" or "polypeptide enzyme" includes full length proteins such as that described by SEQ ID NO: 2 or by a polypeptide having at least 80% sequence similarity or identity to SEQ ID NO: 2, enzymatically active fragments comprising a portion of SEQ ID NO: 2 or a sequence having at least 80% identity or similarity to SEQ ID NO: 2, and polypeptide constructs comprising such enzymatically active polypeptides or polypeptide fragments, e.g., dimers, trimers, multimers, aggregates, and other constructs comprising the enzymatically active polypeptide or polypeptide fragment.

Polypeptides according to the invention which exhibit esterase activity that is resistant to inactivation by agents such as high temperature, high pressure, high salinity, extremes in pH, by the presence of metals, such heavy metals, toxic metals (e.g., biologically metals or metals that inactive other kinds of esterases or lipases), radioactive metals or metal isotopes, may be advantageously used in this method in the presence of these agents.

The enzymatically active polypeptides of the invention may be resistant to inactivation by heat, pH, pressure, salinity and the presence of metals, such as toxic heavy metals, and other substances such as surfactants, detergents or chaotropic agents. The enzymes according to the invention include those that are resistant to inactivation in the presence of surfactants, detergents, or chaotropic agents; those that retain activity within the pH range from 3, 4, 5, 6, 7, 8, and ≥pH 9, preferably between pH 5.5 to 9.0; and those which remain active at salt concentrations ranging from 0, 0.1, 0.25, 0.5, 0.75, 1, 2, 3, 4, 5 to 6M, which ranges include all intermediate subranges and values. Salts include sodium salts (e.g., sodium chloride), potassium salts (e.g., potassium chloride) and salts of divalent cations such as $Mg^{2+}$ or $Ca^{2+}$ (e.g., $MgCl_2$ or $CaCl_2$) as well as other salts found in saline lakes or seas or portions of these having high salinity. Polypeptide enzymes according to the invention also include those which retain activity at temperatures ranging from the freezing point of a solution containing the enzyme to the boiling point of the solution, e.g., from freezing point to 0, 10, 20, 30, 40, 50, 60, 70, 80, 90, 95, 100° C. or boiling point; preferably from 30° C. to 80° C.; enzymes that retain activity under substantially anoxic conditions, and enzymes that retain activity at standard atmospheric pressure 1.013 bars (14.696 psi) or at higher pressures, e.g. suboceanic pressures, e.g., those ranging up to 1,086 bars (15,750 psi).

Polypeptide enzymes according to the invention include those resistant to inactivation by metals. Such metals include heavy metals, biologically toxic metals, metals that inactivate enzymes, and radioactive isotope of a metal is selected from the group consisting of aluminum, antimony, arsenic, barium, beryllium, cadmium, lead, mercury, osmium, thallium, or vanadium; actinium, thorium, uranium, radium, transuranic elements including plutonium and americium, polonium, radioactive isotopes of cobalt, e.g., cobalt-60 and radioactive isotopes of strontium, e.g., strontium-90; chromium, nickel, copper, zinc, and iron. Specifically, heavy metals, a biologically toxic metal, or a radioactive isotope of a metal may be selected from the group consisting of Ca, Mg, Cu, Zn, Co, Mn, Mg, Fe and Ba.

The polypeptide or fragment thereof of disclosed above may be a chimeric protein or a fusion protein that comprises additional fused amino acid residue. Fusion protein constructs may comprise polypeptides from galactosidase, glucuronidase, glutathione-S-transferase, horseradish peroxidase (HRP), chloramphenicol acetyltransferase (CAT), green fluorescent protein (GFP), blue fluorescent protein (BFP) or other fluorescent proteins, or luciferase. Fusion proteins may contain tags such as histidine (His) tags, FLAG tags, influenza hemagglutinin (HA) tags, or other tags to facilitate recovery or purification of the fusion protein. Fusion proteins may contain protein cleavage sites to separate enzyme residues from fusion protein segments.

The polypeptides described herein may be in free form, such as those suspended or dissolved in solution or isolated in solid form, such as in a desiccated or freeze-dried form. They may also be covalently or non-covalently attached to a solid substrate, such as to a glass slide, a plastic slide, a tissue culture plate, a microtiter well, a glass tube, a plastic tube, a bead, including latex, polystyrene, or glass beads, a particle, including a microparticle or a nano particle, a chip, such as a silicon chip or array, or other solid substrate. Kits containing the enzymes of the invention may comprise an isolated or purified enzyme in solution or as a desiccated or freeze-dried product, or a solid substrate to which the enzyme is bound, containers for the enzymes, packaging for a solid substrate, kit packaging materials, a positive control containing a ester or ester-containing product, a negative control, and instructions for use.

The polypeptides and polypeptide fragments described herein having esterase activity as well as cells or fragments of cells containing these polypeptides or polypeptide fragments (including polypeptide constructs such as chimeric or fusion proteins, dimers, trimers, multimers, aggregates, etc.), may form part of an apparatus or bioreactor such as one that treats, processes, transforms, or degrades a substance or compound that is an ester or that contains ester linkages. Such an apparatus may contain in addition to the polypeptide esterases one or more containers or contact surfaces for contacting the esterase or a cell or cellular component containing an esterase with an ester or a substance containing an ester. It may also contain an input and output port for inputting a substrate and remove a treated product. The polypeptide esterases herein resistant to inactivation by metals may be usefully employed in apparatuses containing metal surfaces, particles or other components and those resistant to inactivation at high temperatures, high pressures or in the presence of high salinity, detergents or chaotropic agents may be used an apparatuses which require exposure to these agents.

The polypeptides disclosed herein, including fragments and other polypeptide constructs, may be combined with other ingredients such as a buffer solution, excipient or carrier or preservative that preserves or maintains their enzymatic activity. They may also form part of a composition undergoing processing to remove or transform an ester or ester linkage (e.g., a substrate undergoing processing), a pharmaceutical composition (e.g., a drug or product for treating a disease, disorder or condition associated with the presence of an ester), a cleaner or antiseptic (such as a detergent, surface cleaner, or topical antiseptic), a cosmetic composition (such as a shampoo, mouthwash, or skin treating agent) or a food product (e.g., a dairy product or other food or beverages).

Another aspect of the invention is an antibody and antigen binding fragment of an antibody that binds to the polypeptide or polypeptide fragments (including polypeptide constructs such as chimeric or fusion proteins, multimers, aggregates, etc.). The antibody may be of any isotype, such as IgA, IgD, IgE, IgG, IgM, etc. or may be an antibody construct. It may be a monoclonal, monospecific or polyclonal antibody or a fragment of any of these containing at least one antigen binding site.

The antibody may specifically recognize the polypeptide described by SEQ ID NO: 2 or polypeptide having at least 80% sequence similarity or identity to SEQ ID NO: 2 compared to one or more reference proteins, such as those described by FIG. 2. An antibody may bind to a continuous or discontinuous epitope of the polypeptide of SEQ ID NO: 2 or a polypeptide similar to it. For example, it may recognize an continuous epitope having 6, 7, 8, 9, 10, 11 or 12 contiguous amino acid residues described by SEQ ID NO: 2 or a discontinuous or conformation epitope having 15, 20, 25, 30, 40, 50 or more contiguous residues of SEQ ID NO: 2.

The antibody may be unbound, such as an antibody in solution, or bound covalently or non-covalently to a glass slide, a plastic slide, a tissue culture plate, a microtiter well, a glass tube, a plastic tube, a bead, including latex, polystyrene, or glass beads, a particle, including a microparticle or a nano particle, a chip, such as a silicon chip or array, or other solid substrate. Such antibodies or their fragments may be components of an apparatus such as one that purifies or detects a polypeptide having esterase activity. Methods for producing polyclonal and monoclonal antibodies are well-known in the art. For example, polyclonal antibodies may be produced by immunizing a mammal, such as a mouse, rat, guinea pig, or rabbit with the polypeptide of SEQ ID NO: 2 or an immunogenic fragment thereof optionally with an adjuvant, boosting and recovering antibodies after induction of a secondary immune response. Monoclonal antibodies may be made according to the method of Kohler and Milstein; see Köhler, G.; Milstein, C. (1975). "Continuous cultures of fused cells secreting antibody of predefined specificity". *Nature* 256 (5517): 495-497 which is incorporated by reference.

Another aspect of the invention involves the use of the esterases according to the present invention for enzymatic hydrolysis. This method generally involves contacting a compound or substance that is an ester or that contains an ester linkages with the esterase polypeptides described herein, such as those comprising SEQ ID NO: 2 or having at least 80% sequence similarity or identity with SEQ ID NO: 2 (or their active fragments or polypeptide constructs), for a time and under conditions sufficient for enzymatic hydrolysis of the ester. Polypeptides according to the invention which exhibit esterase activity that is resistant to inactivation by agents such as high temperature, high pressure, high salinity, extremes in pH, by the presence of metals, such heavy metals, toxic metals (e.g., biologically metals or metals that inactive other kinds of esterases or lipases), radioactive metals or metal isotopes, may be advantageously used in this method in the presence of these agents.

Such metals include heavy metal, a biologically toxic metal, or a radioactive isotope of a metal is selected from the group consisting of aluminum, antimony, arsenic, barium, beryllium, cadmium, lead, mercury, osmium, thallium, or vanadium; actinium, thorium, uranium, radium, transuranic elements including plutonium and americium, polonium, radioactive isotopes of cobalt, e.g., cobalt-60 and radioactive isotopes of strontium, e.g., strontium-90; chromium, nickel, copper, zinc, and iron. Specifically, heavy metals, a biologically toxic metal, or a radioactive isotope of a metal may be selected from the group consisting of Ca, Mg, Cu, Zn, Co, Mn, Mg, Fe and Ba.

The polypeptide enzymes according to the invention also include those that are resistant to inactivation in the presence of surfactants, detergents, chaotropic agents or other known enzyme or esterase inhibitors; those that retain activity within the pH range from 3, 4, 5, 6, 7, 8, and ≥pH 9, preferably between pH 5.5 to 9.0; and those which remain active at salt concentrations ranging from 0, 1, 2, 3, 4, 5 to 6M. Salts include sodium salts (e.g., sodium chloride), potassium salts (e.g., potassium chloride) and salts of divalent cations such as $Mg^{2+}$ or $Ca^{2+}$ (e.g., $MgCl_2$ or $CaCl_2$) as well as other salts found in saline lakes or seas or portions of these having high salinity. Polypeptide enzymes according to the invention also include those which retain activity at temperatures ranging from the freezing point of a solution containing the enzyme to the boiling point of the solution, e.g., from freezing point to 0, 10, 20, 30, 40, 50, 60, 70, 80, 90, 95, 100° C. or boiling point; preferably from 30° C. to 80° C.; enzymes that retain activity under substantially anoxic conditions, and enzymes that retain activity at standard atmospheric pressure 1.013 bars (14.696 psi) or at higher pressures, e.g. suboceanic pressures, e.g., those ranging up to 1,086 bars (15,750 psi).

In one advantageous embodiment the enzyme according to the invention has lipase/esterase activity at a temperature ranging from 45-75° C. and retains this activity even at 80° C. It exhibits high activity under alkaline conditions and maximum activity in a sodium chloride solution at a concentration of 2M NaCl. This embodiment is resistant to inactivation by Ca, Mg, Cu, Zn, Co, Mn, Mg, Fe and Ba. It is active on short chain esters, especially in cleaving acetyl esters, but also exhibits activity against 4-carbon esters and 6-carbon esters and it lacks substantial activity on longer chain esters and thus can be subclassified as an esterase.

Other aspects of the invention include the following.

A method for processing a food comprising contacting the food, nutraceutical, sweetener, or a flavoring with an enzyme or polypeptide enzyme according to the invention or with a cell expressing said enzyme or polypeptide enzyme under conditions suitable for partial or complete cleavage of esters in said food or flavoring, such as cleavage of long chain esters into short chain esters, or under conditions suitable to improve the organoleptic or nutritional properties of the food or flavoring.

A method for processing, transforming, degrading or recycling an organic material, such as leather, cellulose, wood pulp, or paper, comprising contacting the organic material with an enzyme or polypeptide enzyme according to the invention or with a cell expressing said enzyme or polypeptide enzyme under conditions suitable for partial or complete cleavage of esters in the organic material. Such a method may be applied for bulk solubilization of biomass.

A method for processing, transforming, degrading or recycling a synthetic material, such as a plastic containing ester linkages, comprising contacting the synthetic material with an enzyme or polypeptide enzyme according to the invention or with a cell expressing said enzyme or polypeptide enzyme under conditions suitable for partial or complete cleavage of esters in synthetic material.

A method for processing, transforming, or refining a biofuel or a petrochemical, such as crude oil or other fuel stock that contains esters, comprising contacting the petrochemical with an enzyme or polypeptide enzyme according to the invention or with a cell expressing said enzyme or polypeptide enzyme under conditions suitable for partial or complete cleavage of esters in synthetic material.

A method for processing a chemical substrate that contains esters as well as metals or salts, comprising contacting the chemical substrate with an enzyme or polypeptide enzyme according to the invention or with a cell expressing said enzyme or polypeptide enzyme under conditions suitable for partial or complete cleavage of esters in the chemical substrate. A chemical substrate may be one used to produce a pharmaceutical product, a nutraceutical, a bulk chemical, or a fine chemical.

A method for processing waste material that contains esters and optionally metals and/or salts, comprising contacting the waste with an enzyme or polypeptide enzyme according to the invention or with a cell expressing said enzyme or polypeptide enzyme under conditions suitable for partial or complete cleavage of esters in the waste material. Other products and methods of use as described in the background section above are also specifically contemplated.

EXAMPLES

Example 1. Sample Collection, DNA Isolation and Fosmid Library Construction

Water samples were collected from Atlantis II brine lower convective layer (LCL) during the KAUST Red Sea 2010 expedition (Latitude (N) 21° and Longitude (E) 38°). Collected water samples were immediately processed by serial filtration on mixed Cellulose Esters filters (Nitrocellulose/Cellulose Acetate) with pore sizes of 3, 0.8 and 0.1 μm. Filters were stored in sucrose buffer followed by DNA extraction. DNA extraction was carried out using the Epicentre Metagenomic DNA Isolation Kit for Water, from the 0.1 μm filters. Fosmid library construction was carried out using Copy Control Fosmid Library Production Kit (Epicentre), in which the metagenomic DNA was sheared, size selected of ~40 kb size DNA fragments and subsequently cloned into fosmids and transformed into E. coli host cells. The constructed library (fosmid vector pCC2FOS) was spread over 11 large petri dish plates. Then colonies were picked individually and each colony was transferred to one well of the 96 well ELISA plates, such that each well contains only one fosmid. The result was a total of 11196 well ELISA plates with total of 10,656 clones.

Results. Screening Metagenomic Library for Lipolytic Activity

The constructed fosmid library comprised 10,656 clones that were manually placed into 111 96-well plates for ease of handling. Functional screening of the fosmid library on tributyrin agar detected a total of five recombinant clones forming a clear halo zone indicative of putative lipolytic activity.

Example 2. Functional Screening for Lipolytic Activity, Sequencing and Identification of Lipolytic Gene Transformants were grown on LB agar plates supplemented with 12.5 .mu.g chloramphenicol/ml and 1% Tributyrin (Sigma-Aldrich). Plates were incubated at 37.degree. C. for 3 days and the appearance of a clear halo zone around a transformant was indicative of a candidate lipolytic activity. Candidate transformants were selected for fosmid isolation using the WIZARD™. Plus SV Minipreps DNA Purification System (Promega).

Fosmids were digested using BamHI to assess their diversity (data not shown) and subjected to pyrosequencing using the GS FLX Titanium pyrosequencer (454 Life Sciences). Table 1a summarizes the pyrosequencing data. Sequences obtained were assembled using GS FLX de novo assembler. Open reading frames (ORFS) were identified using the ORF Finder tool (available on the world wide web at ncbi.nlm.nih.gov/gorf/gorf.html) provided by the National Center for Biotechnology Information (NCBI). The putative function of each ORF was annotated by comparing the amino acid sequences to the non-redundant protein database using BLASTP.

TABLE 1A

Characteristics of 454 pyrosequencing data

| | |
|---|---|
| Total Number of Reads | 31767 |
| Total Number Of Bases | 7755522 |
| Number of Aligned Reads | 28166 (88.66%) |
| Number of Aligned Bases | 6936553 (89.44%) |
| All Contig Metrics | |
| Number Of Contigs | 11 |
| Number Of Bases | 107205 |
| Large Contig Metrics | |
| Number Of Contigs | 4 |
| Number Of Bases | 90337 |

TABLE 1A-continued

Characteristics of 454 pyrosequencing data

| | |
|---|---|
| Average Contig Size (bp) | 22584 |
| Largest Contig Size (bp) | 32374 |

Example 3. Sequence Analysis and Phylogenetic Tree Construction

Domain search was conducted by the Conserved Domain (CD)-search tool provided by NCBI (available on the world wide web at ncbi.nlm.nih.gov/Structure/cdd/wrpsb.cbi). Prediction of signal peptide sequence was performed using SignalP 3.0 servers. For phylogenetic analysis, sequences of 43 bacterial lipolytic enzymes (representing the eight families of bacterial lipolytic enzymes as classified by Arpigny & Jaeger, 1999.sup.17) were retrieved from the GenBank sequence database. The selected 43 enzymes are present in FIG. 3. Multiple sequence alignment of retrieved sequences and EstATII was performed using ClustalW version 1.83.sup.18. Phylogenetic tree was constructed using the neighbor-joining method using the software MEGA version 5.05.sup.19. Bootstrapping (10,000 replicates) was used to estimate the confidence of the tree.

Results: Sequencing, Identification and Sequence Analysis

Fosmids of the five positive recombinant clones were pyrosequenced to identify the genes responsible for putative lipolytic activity. Following assembly, four large contigs (>10 kb) and seven smaller contigs (ranging from 1.4-4.9 kb) were obtained; the largest contig obtained being approximately 32 kb (Table 1b). A 945 bp ORF encoding a putative esterase/lipase (designated EstATII) was identified.

TABLE 1B

Contigs generated from 454 pyrosequencing data and utilized in this study.

| Contig # | Length (bp) | Number of Aligned Reads |
|---|---|---|
| 1 | 32374 | 5647 |
| 2 | 23734 | 2626 |
| 3 | 21070 | 5060 |
| 4 | 13159 | 10136 |
| 5 | 4915 | 977 |
| 6 | 4767 | 2319 |
| 7 | 1606 | 1074 |
| 8 | 1431 | 22 |
| 9 | 1407 | 23 |
| 10 | 1403 | 21 |
| 11 | 1339 | 49 |

The maximum identity to sequences in the database was 65% with an alpha/beta hydrolase domain-containing protein from *Pseudomonas mendocina*. The highest identity to a lipolytic enzyme in the database was 56% to an esterase from *Pseudomonas aeruginosa*. EstATII was the only lipolytic enzyme detected, however other ORFs encoding for sulfatases were detected which could be responsible for false positive activity as previously reported[22]. EstATII consists of 945 bp corresponding to 314 amino acids. A domain search conducted using CD-search tool detected an alpha/beta hydrolase fold domain [Pfam ID: pfam07859] between residues 85 and 286, which is the catalytic domain found in members of the alpha/beta hydrolases family. An esterase/lipase domain (cd00312) was also detected. In addition, two prokaryotic Clusters of Orthologous Groups (COGs) were identified; COG0657 and COG2272 which are involved in lipid metabolism.

The catalytic triad residues were identified in EstATII; Ser160, Asp204 and His282. The catalytic nucleophilic residue Ser160 was found in the consensus pentapeptide GDSAG (SEQ ID NO:8), which is characteristic of the hormone sensitive lipase (HSL) family. Another motif characteristic of the HSL family (HGG), which contributes to the formation of the oxyanion hole, was also identified in the sequence (FIG. 2). EstATII was predicted to be soluble since a signal peptide was not detected. A transmembrane domain was identified using TMAP program[23]. This domain is a stretch of 24 amino acids at N-terminal site from amino acid 29-52 (data not shown). The membrane imbedded domain was repeatedly reported in other identified esterase[24].

Bacterial lipolytic enzymes were classified into eight families by Arpigny & Jaeger in 1999[17]. In order to determine whether EstATII classifies as a member of one of these families, a multiple sequence alignment of EstATII together with 43 sequences of bacterial lipolytic enzymes, representing the eight families, was performed. A phylogenetic tree was constructed and EstATII grouped with members of family IV which is also known as the HSL family (FIG. 3).

Example 4. Cloning of EstATII Gene

The gene was amplified using the forward primer (EstF) 5'-ATG TCC AGG TAC GTT GAT GAG C-3' (SEQ ID NO: 3) and the reverse primer (EstR) 5'-TCA GCT TAC CGA GTC GGT CT-3' (SEQ ID NO: 4) using Taq polymerase (Fermentas). The primers were designed based on a 945 bp ORF in Contig 1 (Table 1-b), which was annotated as a putative lipolytic sequence by BlastP. The amplified fragment was cloned into the pET-SUMO vector (CHAMPION™ pET SUMO Protein Expression System kit, Invitrogen) according to manufacturer's instructions. Recombinant plasmids were transformed into *E. coli* BL21 (DE3) chemical competent cells. Colony PCR using the gene primers was performed to verify the presence of the insert, while colony PCR using the gene forward primer and the vector reverse primer was performed to verify the orientation of the gene.

Example 5. Overexpression and Purification of Recombinant EstATII Enzyme 200 ml of *E. coli* BL21 (DE3) harboring the pET-SUMO/EstATII plasmid were grown in LB at 37° C. until the culture reached an $OD_{600}$=0.4-0.6. The culture was induced by adding isopropyl-b-D thiogalactopyranoside (IPTG) to a final concentration of 0.5 mM and further incubated for 3 hours at 37° C. The cells were harvested by centrifugation at 10,000.times.g for 15 min at 4° C. The purification procedure was performed using the His SPINTRAP™ (GE Healthcare) according to manufacturer's instructions. The purified protein was dialysed against 50 mM $NaH_2PO_4$ buffer, pH 8.0, analyzed by SDS-PAGE and stored at 4° C. until further use. Protein isolation was confirmed by Western Blot analysis using an anti-His-G antibody (Invitrogen).

Results: Overexpression and Purification of EstATII

In order to investigate the biochemical characteristics of EstATII, the gene was expressed as an N-terminal His-tag recombinant protein in the expression vector pET-SUMO in *E. coli* BL21 (DE3) cells. The overexpressed protein had the expected molecular weight of approximately 46 kDa and western blot analysis of the purified protein showed a single band at the expected size (FIG. 4).

Example 6. Characterization of EstATII

Enzyme activity was determined by measuring the formation of p-nitrophenol (pNP) from the enzymatic hydrolysis of the p-nitrophenyl ester; p-nitrophenyl butyrate (Sigma-Aldrich). The reaction mixture contained p-nitrophenyl butyrate (pNPB) to a final concentration 0.1 mM and 50 mM Tris-HCl pH=8. In this study, the standard reaction was conducted at 65° C., initiated by the addition of EstATII and terminated by the addition of 10% SDS. Measurements were done at 410 nm using UV-spectrophotometer (Ultrospec 3100 pro, Amersham Biosciences) unless stated otherwise[20]. All experiments were performed in triplicates. Substrate specificity of EstATII was determined using p-nitrophenol esters with varying side chain length. Short-chain fatty acid esters used were PNP-acetate (C2), PNP-butyrate (C4) and PNP-valerate (C5) and long-chain fatty acid esters used were PNP-decanoate (C10), PNP-dodecanoate C12, PNP-myristate (C14) and PNP-palmitate (C16). The optimum temperature for the activity of EstATII was determined at a temperature range 30-80° C. The optimum pH for the activity of EstATII was measured at a pH range (3-9.5) using the following buffers: 50 mM sodium acetate (pH 3-5.5), 50 mM sodium phosphate (pH 6, 7.5) and 50 mM Tris-HCL (pH 7.5-9.5). Formation of pNP was measured at 348 nm (the pH-independent isosbestic wavelength of pNP)[21]. The effect of NaCl concentration on enzyme activity was measured at different NaCl concentrations (0-4.5 M) under standard assay conditions. To assess the effect of metal ions on enzyme activity, cations were added to a final concentration of 1 mM, and relative activity measured at the above-described standard conditions. The effect of detergents (at final concentrations 0.1 and 1%) and inhibitors (final concentration 1 mM) on enzyme activity was tested at the above-described standard assay conditions.

Results: Biochemical Characterization of EstATII

Effect of Temperature and pH on the Activity of EstATII

The effect of temperature on the activity of EstATII was assayed at temperatures ranging from 30° C. to 80° C. The activity of the enzyme increased reproducibly with the increase in temperature until 65° C., after which the activity started to drop. High activity of the enzyme (>70%) was observed at temperatures ranging from 45° C. to 75° C. The apparent optimum temperature of EstATII is 65° C. The enzyme remained active even after reaching 80° C. (Table 2).

The effect of pH on the activity of EstATII was assayed at pH range 3-9. The enzyme exhibited significant activity (>50%) at pH=7-9, with the highest activity at pH=8.5. No activity was observed at pH lower than 5.5 (Table 2).

Effect of NaCl Concentration on the Activity of EstATII

The activity of EstATII was assayed at different molar concentrations of NaCl ranging from 0M-4.5M. The enzyme showed highest activity in the presence of 2M NaCl. Enzyme activity was maintained up to 4.5M NaCl (Table 2).

Substrate Specificity of EstATII

To assess whether EstATII is a lipase or an esterase, its substrate specificity was investigated using an array of p-nitrophenol esters with varying chain length. EstATII was active towards short-chain fatty acid esters (C2, C4 and C5), however, under the conditions it showed no activity towards long-chain fatty acid esters (C10, C12, C14 and C16) indicating that EstATII is an esterase not a lipase[25] (Table 2). However, these results do not preclude activity on other substrates, such as longer chain fatty acid esters under different conditions, such as conditions found in extreme environments such as deep sea brine pools. Biocatalysts such as EstATII-type esterases often reflect the conditions of the environment from which they were isolated and therefore can be potentially used for industrial and biotechnological applications that employ extreme conditions.

Effect of Metal Ions on the Activity of EstATII

The effect of metal ions was assessed with and without EDTA chelation. Enzyme activity was not affected by EDTA chelation, suggesting that EstATII is not a metalloenzyme[9]. Enzyme activity was promoted by Barium (158%), Manganese (111%) and Cobalt (104%). The enzyme was resistant to inhibition by the rest of the metal ions tested; activity remained above 60% (Table 3). Upon investigating the effect of heavy metal ions on the activity of EstATII in comparison to other esterases (thermophilic and mesophilic), it was noticed that Copper, Zinc and Mercury exhibit a strong inhibitory effect on the activity of most esterases included in the comparison (<50%) (Table 3). Although EstATII shows significant resistance to all heavy metal ions tested, resistance to these three heavy metals is of particular interest due to their strong inhibitory effect on most identified esterases.

TABLE 3

Activity of Mesophilic and Thermophilic Esterase in comparison to the Red Sea EstAII activity

| | | Temp ° C. | pH | $Ca^{2+}$ | $Mg^{2+}$ | $Cu^{2+}$ | $Zn^{2+}$ |
|---|---|---|---|---|---|---|---|
| Thermophilic | EstATII | 65 | 8.5 | 94.8 ± 3 | 90.6 ± 3.6 | 94.8 ± 0.1 | 85.2 ± 4.4 |
| | G. obscurus | 80 | 8 | 91.7 | 100 | 76.9 | 43.9 |
| | LKE-028 | 70 | 11 | 167.7 | 173.3 | 94.1 | 43.6 |
| | EstA3 | 70 | 9.5 | 80.3 | 82.8 | 24.9 | 37.1 |
| | EstA | 60-65 | 9.5 | 152 | 170 | N/A | 17 |
| | EstCS2 | 55 | 9 | 119 | N/A | N/A | N/A |
| | DR8806 | 50 | 8 | 64.5 | 60.7 | 34.9 | 26 |
| | A. gonensis A4 | 60-80 | 5.5 | 86 ± 4 | N/A | 69 ± 3 | 59 ± 4 |
| | EstR | 60 | 9 | 87 | 87 | 93 | 87 |
| | EstY | 50 | 9 | ~90 | N/A | N/A | ~15 |
| | Fusarium | 50 | 8 | 96.6 ± 2.6 | 94.9 ± 2.7 | 11.7 ± 0.4 | 75.2 ± 1.0 |
| Mesophilic | EstIM1 | 40° C. | 8 | 95 | 88 | 76 | 18 |
| | Est_p1 | 40° C. | 8.57 | 86.5 ± 1 | 101 ± 0.03 | 11.3 ± 2 | 24.6 ± 5 |
| | EstAS | 35° C. | 9 | 100.5 ± 3.4 | 81.7 ± 2.9 | 7.8 ± 2.3 | 114.7 ± 1.3 |
| | EstA | 45° C. | 6.5 | 102.9 ± 6.7 | 139.5 ± 7.8 | 99.3 ± 8.1 | 89.7 ± 8.7 |
| | EstB | 45° C. | 7.5 | 107.6 ± 8.3 | 86.1 ± 6.4 | 27.2 ± 2.3 | 11.4 ± 1.1 |
| | EstEH112 | 35° C. | 8 | 102 | 102 | 97 | 96 |
| | EstPc | 35° C. | 8.5 | N/A | 94 | 49 | 0.80 |

TABLE 3-continued

Activity of Mesophilic and Thermophilic Esterase in comparison to the Red Sea EstAII activity

|  |  |  |  |  |  |  |  |
|---|---|---|---|---|---|---|---|
|  | rEst97 | 35° C. | 7.5 | 96.4 ± 6.3 | 96.7 ± 2.8 | 68.3 ± 3.3 | 7.4 ± 0.5 |
|  | HBB-4 | N/A | N/A | 102.9 ± 0.29 | 93.21 ± 1.56 | 10.78 ± 1.46 | N/A |
|  | EstKT4 | 40° C. | 8.5 | 83 | 81 | 68 | 38 |
|  | EstKT7 | 35° C. | 8 | 68 | 75 | 25 | 22 |
|  | EstKT9 | 45° C. | 8.5 | 90 | 96 | 77 | 26 |
|  | EstC | 35 | 8.5-9 | 88 + 1 | 93 + 0.6 | 75 + 0.1 | 18 + 1 |

|  |  | $Co^{2+}$ | $Mn^{2+}$ | $Hg^{2+}$ | $Fe^{3+}$ | $Ba^{2+}$ | Ref. |
|---|---|---|---|---|---|---|---|
| Thermo-philic | EstATII | 104 ± 2 | 111.8 ± 0.1 | 60.9 ± 0.4 | 96.2 ± 0.7 | 158.3 ± 2.2 |  |
|  | G. obscurus | 114.9 | 97.4 | 49.9 | N/A | N/A | 26 |
|  | LKE-028 | 124.7 | N/A | 89.3 | 84.4 | 33.9 | 27 |
|  | EstA3 | 61.8 | 66.6 | 31.3 | 54.1 | N/A | 38 |
|  | EstA | N/A | N/A | N/A | N/A | N/A | 39 |
|  | EstCS2 | N/A | N/A | N/A | N/A | N/A | 29 |
|  | DR8806 | N/A | 47.1 | 21.9 | N/A | N/A | 28 |
|  | A. gonensis A4 | 65 ± 5 | 96 ± 4 | 47 ± 2 | N/A | N/A | 40 |
|  | EstR | N/A | 95 | N/A | 73 | N/A | 35 |
|  | EstY | N/A | N/A | N/A | ~40 | N/A | 30 |
|  | Fusarium | 98.1 ± 1.4 | 91.9 ± 2.6 | 38.4 ± 1.5 | N/A | N/A | 41 |
| Mesophilic | EstIM1 | 87 | 90 | 8 | N/A | 84 | 33 |
|  | Est_p1 | 79.6 ± 14 | 85.5 ± 3 | N/A | N/A | N/A | 34 |
|  | EstAS | 117.8 ± 2.1 | 192.9 ± 3.8 | N/A | N/A | N/A | 9 |
|  | EstA | 116.5 ± 6.6 | 142.8 ± 9.5 | N/A | N/A | N/A | 36 |
|  | EstB | 116 ± 7.2 | 88.7 ± 4.9 | N/A | N/A | N/A | 36 |
|  | EstEH112 | 102 | 101 | N/A | N/A | N/A | 37 |
|  | EstPc | 93 | 121 | N/A | N/A | N/A | 31 |
|  | rEst97 | 80.4 ± 4.3 | 97.1 ± 3.3 | N/A | 71.4 ± 9.9 | N/A | 42 |
|  | HBB-4 | 84.11 ± 1.33 | 159.7 ± 3.31 | 3.41 ± 0.28 | 72.07 ± 1.13 | N/A | 43 |
|  | EstKT4 | 57 | 27 | N/A | N/A | N/A | 44 |
|  | EstKT7 | 115 | 65 | N/A | N/A | N/A | 44 |
|  | EstKT9 | 78 | 92 | N/A | N/A | N/A | 44 |
|  | EstC | 56 + 1 | 88 + 1 | N/A | N/A | N/A | 32 |

Effect of Detergents, Reducing and Modifying Agents on the Activity of EstATII

The effect of detergents (ionic and non-ionic) was tested at two concentrations: 0.1% and 1%. At 0.1%, Tween 80 showed no effect on enzyme activity. Triton X-100 and Tween 20 were tolerated by the enzyme (42.3% and 87.5% respectively), while SDS dramatically inhibited enzyme activity to 6%. At 1%, EstATII was tolerant to the effects of Tween 20 and 80 (40.1% and 54.5% respectively), while SDS and Triton X-100 abolished enzyme activity. Reducing agent β-mercaptoethanol (at final concentration 1 mM) enhanced enzyme activity to 117.9%, while 1 mM DTT slightly inhibited activity to 78.9%. DEPC, the histidine residue modifier, reduced activity by half. This result is in agreement with the involvement of a histidine residue in the catalytic triad (Table 2).

TABLE 2

Effect of Temperature, pH, substrate chain length and some additives on EstATII activity

| Variable | Relative Activity |
|---|---|
| Temperature (° C.) | |
| 30 | 56.3 ± 0.8 |
| 35 | 59.9 ± 1 |
| 40 | 65.3 ± 1.8 |
| 45 | 86.9 ± 0.9 |
| 50 | 90.9 ± 2 |
| 55 | 93.9 ± 1 |
| 60 | 95.9 ± 0.3 |
| 65[a] | 100 ± 0.2 |
| 70 | 91.6 ± 0.15 |
| 75 | 76.7 ± 0.3 |
| 80 | 46.7 ± 1.3 |
| pH | |
| 3 | 0 |
| 4 | 0 |
| 5 | 0 |
| 5.5 | 13.1 ± 0.2 |
| 6 | 38.5 ± 1.2 |
| 6.5 | 43.2 ± 2 |
| 7 | 81.5 ± 1 |
| 7.5 (Na Phosphate) | 88 ± 1 |
| 7.5 (Tris.HCl) | 66.1 ± 0.2 |
| 8 | 84.7 ± 1.1 |
| 8.5[a] | 100 ± 3 |
| 9 | 60 ± 2 |
| Substrate Specificity | |
| pNP-acetate (C2) | 100 ± 3 |
| pNP-butyrate (C4) | 61.9 ± 0.8 |
| pNP-valerate (C5) | 40.5 ± 1.2 |
| pNP-decanoate (C10) | 0 |
| pNP-dodecanoate (C12) | 0 |
| pNP-myristate (C14) | 0 |
| pNP-palmitate (C16) | 0 |
| Sodium Chloride[b] | |
| 0.5M | 102.2 ± 2 |
| 1M | 99.9 ± 0.5 |
| 1.5M | 120 ± 1 |
| 2M | 122.9 ± 1 |
| 2.5M | 102.4 ± 1.8 |
| 3M | 73.8 ± 3.8 |

TABLE 2-continued

Effect of Temperature, pH, substrate chain length and some additives on EstATII activity

| Variable | Relative Activity |
|---|---|
| 3.5M | 65.3 ± 4.6 |
| 4M | 53.8 ± 1 |
| 4.5M | 39.7 ± 1.7 |
| Detergents (0.1%) | |
| SDS | 6.1 ± 0.4 |
| Triton X-100 | 42.2 ± 1.1 |
| Tween 20 | 87.5 ± 2.3 |
| Tween 80 | 100.7 ± 2.3 |
| Detergents (1%) | |
| SDS | 0 |
| Triton X-100 | 4.3 ± 1 |
| Tween 20 | 40.1 ± 0.9 |
| Tween 80 | 54.5 ± 0.7 |
| Reducing and Modifying agents (1 mM) | |
| β-mercaptoethanol | 117.9 ± 0.3 |
| DTT | 78.9 ± 4.2 |
| DEPC | 48 |
| CTAB | 13.1 ± 1.9 |

[a]Optimum condition (defined as 100%)
[b]Activity in the absence of NaCl is defined as 100%

As shown above, the inventors have identified a novel esterase (EstATII) from the Atlantis II brine pool in the Red Sea, using a function-based approach. Sequence and phylogenetic analysis of EstATII revealed that it is a new member of the Hormone-Sensitive Lipase family (Family IV). EstATII groups with members of the HSL family and was found to harbor conserved motifs characteristic of this family. Characterization of EstATII reflected the environment from which it was isolated; shows that it is thermophilic with an optimum temperature 65° C. and halotolerant maintaining significant activity (>50%) up to 4M NaCl.

In addition and of particular interest, EstATII shows significant resistance to inhibition by all heavy metal ions tested in this work ($Ca^{2+}$, $Mg^{2+}$, $Cu^{2+}$, $Zn^{2+}$, $Co^{2+}$, $Mn^{2+}$, $Mg^{2+}$, $Fe^{3+}$ and $Ba^{2+}$). In this aspect, EstATII was compared to 23 recently characterized esterases of both thermophilic and mesophilic nature. They represent different families and are isolated from either a single isolate or a metagenomic library. These include selected thermophilic esterases from G. obscurus[26], Rhodococcus sp. LKE-028[27], Bacillus subtilis DR8806[28], as well as, EstCS2 from compost soil metagenomic library[29] and EstY from metagenomic library of Yangtze River[30]. Examples of mesophilic esterases selected for this comparison include EstPc, a cold-adapted esterase from Psychrobacter cryohalolentis K5T[31], EstC; a cold-active esterase from Streptomyces coelicolor A3(2)[32], as well as, EstIM1 from a metagenomic library of mountain soil[33] and Est_p1 from a metagenomic library of neritic sediments of the South China sea[34]. In our comparison, an enzyme was considered significantly inhibited by a given heavy metal ion, if its relative activity dropped below 50%. It was found that most esterases included for comparison were significantly inhibited by three of the tested metal ions; Copper, Zinc and Mercury. Copper significantly inhibited 37.5% of thermophilic esterases and 46% of mesophilic esterases (~43% of all esterases). Zinc inhibited 60% of thermophilic esterases and 75% of mesophilic esterases (~68% of all esterases). Mercury significantly inhibited ~71.5% of thermophilic esterases and 100% of mesophilic esterases (~78% of all esterases). 19 out of the 23 esterases discussed in our analysis exhibited significant inhibition by at least one of the three heavy metal ions. Only 4 esterases showed resistance to inhibition by all metal ions tested; EstATII (this study), EstR (isolated from Ralstonia sp. M1)[35], EstA (isolated from a metagenomic library of the South China sea)[36] and EstH112 (isolated from the metagenome of a Korean intertidal flat sediment)[37]. Some comparisons using certain metals, detergents and/or inhibitors were not made since they were not performed in prior studies. The demonstrated resistance of EstTAII to inhibition by metal ions, in addition to retention of significant activity when exposed to some of the detergents and inhibitors tested, show that EstATII-like esterases are useful biocatalyst under conditions adverse to enzymatic activity of other esterases.

INCORPORATION BY REFERENCE

Each document, patent, patent application or patent publication cited by or referred to in this disclosure is incorporated by reference in its entirety especially for describing the subject matter surrounding the citation of the reference in the text. However, no admission is made that any such reference constitutes background art and the right to challenge the accuracy and pertinence of the cited documents is reserved.

REFERENCES

1. Qian, P. Y. et al. Vertical stratification of microbial communities in the Red Sea revealed by 16S rDNA pyrosequencing. *ISME J* 5, 507-18 (2010).
2. Antunes, A., Ngugi, D. K. & Stingl, U. Microbiology of the Red Sea (and other) deep-sea anoxic brine lakes. *Environmental Microbiology Reports* 3, 416-433 (2011).
3. Bower, A. S. R/V Oceanus Voyage 449-6 Red Sea Atlantis II Deep Complex Area. *Woods Hole Oceanog. Instil. Technical Report*, WHOI-KAUST-CTR-2009-01 (2009).
4. Lorenz P. & Eck J. Metagenomics and industrial applications. *Nature Reviews Microbiology* 3, 510-516 (2005).
5. Uchiyama T. & Miyazaki K. Functional metagenomics for enzyme discovery: challenges to efficient screening. *Current Opinion in Biotechnology* 20, 616-622 (2009).
6. Schmeisser C., Steele H. & Streit W. R. Metagenomics, biotechnology with non-culturable microbes. *Applied Microbiology and Biotechnology* 75, 955-962 (2007).
7. Jeon, J. H. et al. Novel lipolytic enzymes identified from metagenomic library of deep-sea sediment. *Evid Based Complement Alternat Med* 2011, 271419 (2011).
8. Glogauer, A. et al. Identification and characterization of a new true lipase isolated through metagenomic approach. *Microb Cell Fact* 10, 54 (2011).
9. Zhang, T. & Han, W. J. Gene cloning and characterization of a novel esterase from activated sludge metagenome. *Microb Cell Fact* 8, 67 (2009).
10. Steele H. L., Jaeger K. E., Daniel R & Streit W. R. Advances in Recovery of Novel Biocatalysts from Metagenomes. *Journal of Molecular Microbiology and Biotechnology* 16, 25-37 (2009).
11. Salameh M. & Wiegel J. Lipases from extremophiles and potential for industrial applications. *Applied and Environmental Microbiology* 61, 253-283 (2007).
12. Hasan F., Shah A. A. & Hameed A. Industrial applications of microbial lipases. *Enzyme and Microbial Technology* 39 235-251 (2006).
13. Aravindan R., Anbumathi P. & Viruthagiri T. Lipase applications in food industry. *Indian Journal of Biotechnology* 6, 141-158 (2007).

14. Gandhi N. N. Applications of Lipase. *Journal of the American Oil Chemists' Society* 74, 621-634 (1997).
15. Hata K., Matsukura M., Taneda H. & Fujita Y. in Enzymes for Pulp and Paper Processing 280-296 (American Chemical Society, 1996).
16. Rusch, D. B. et al. The Sorcerer II Global Ocean Sampling expedition: northwest Atlantic through eastern tropical Pacific. *PLoS Biol* 5, e77 (2007).
17. Arpigny J. L. & Jaeger K. E. Bacterial lipolytic enzymes: classification and properties. *Journal of Biochemistry* 343, 177-183 (1999).
18. Thompson, J. D., Higgins, D. G. & Gibson, T. J. CLUSTAL W: improving the sensitivity of progressive multiple sequence alignment through sequence weighting, position-specific gap penalties and weight matrix choice. *Nucleic Acids Res* 22, 4673-80 (1994).
19. Tamura, K. et al. MEGA5: molecular evolutionary genetics analysis using maximum likelihood, evolutionary distance, and maximum parsimony methods. *Mol Biol Evol* 28, 2731-9 (2011).
20. Henne, A., Schmitz, R. A., Bomeke, M., Gottschalk, G. & Daniel, R. Screening of environmental DNA libraries for the presence of genes conferring lipolytic activity on *Escherichia coli*. *Appl Environ Microbiol* 66, 3113-6 (2000).
21. Rhee, J. K., Ahn, D. G., Kim, Y. G. & Oh, J. W. New thermophilic and thermostable esterase with sequence similarity to the hormone-sensitive lipase family, cloned from a metagenomic library. *Appl Environ Microbiol* 71, 817-25 (2005).
22. Litthauer D., Abbai N. S., Piater L. A. & van Heerden E. Pitfalls using tributyrin agar screening to detect lipolytic activity in metagenomic studies. *African Journal of Biotechnology* 9, 4282-4285 (2010).
23. Persson B & Argos P. Prediction of transmembrane segments in proteins utilising multiple sequence alignments. *Journal of Molecular Biology* 237, 182-92 (1994).
24. Wijeyesakere S J, Richardson R J & Stuckey J A. Modeling the tertiary structure of the patatin domain of neuropathy target esterase. *The Protein Journal* 26, 165-72. (2007).
25. Hausmann S. & Jaeger K. E. in Handbook of Hydrocarbon and Lipid Microbiology 1100-1126 (Springer-Verlag Berlin Heidelberg, 2010).
26. Atef Jaouani et al. Purification and characterization of a highly thermostable esterase from the actinobacterium Geodermatophilus obscurus strain G20. *Journal of Basic Microbiology*, 1-8 (2012).
27. Lokendra Kumara, Balvinder Singhb, Dilip Kumar Adhikaric, Joydeep Mukherjeed & Ghoshc, D. A thermoalkaliphilic halotolerant esterase from *Rhodococcus* sp. LKE-028 (MTCC 5562): Enzyme purification and characterization. *Process Biochemistry* 47 (2012).
28. Ahmad Asoodeha & Ghanbarib, T. Characterization of an extracellular thermophilic alkaline esterase produced by *Bacillus subtilis* DR8806 *Journal of Molecular Catalysis B: Enzymatic* 85, 49-55 (2013).
29. Chul-Hyung Kang et al. A novel family VII esterase with industrial potential from compost metagenomic library. *Microbial Cell Factories* 10 (2011).
30. Chao Wu & Sun, B. Identification of Novel Esterase from Metagenomic Library of Yangtze River. *Journal of Microbiology and Biotechnology* 19, 187-193 (2009).
31. Ksenia Novototskaya-Vlasova, Lada Petrovskaya, Sergey Yakimov & Gilichinsky, D. Cloning, purification, and characterization of a cold-adapted esterase produced by *Psychrobacter cryohalolentis* K5T from Siberian cryopeg. *FEMS Microbiol Ecol*, 1-9 (2012).
32. Guillaume Brault, François Shareck, Yves Hurtubise, François Lépine & Doucet, N. Isolation and Characterization of EstC, a New Cold-Active Esterase from *Streptomyces coelicolor* A3(2). *PLoS One*7 (2012).
33. Kyong-Cheol Ko et al. Identification and characterization of a novel cold-adapted esterase from a metagenomic library of mountain soil. *Journal of Industrial Microbiology and Biotechnology*, 681-689 (2012).
34. Qing Peng et al. A novel esterase gene cloned from a metagenomic library from neritic sediments of the South China Sea. *Microbial Cell Factories* 10 (2011).
35. Quyen D T, Dao T T & S L, T. N. A novel esterase from *Ralstonia* sp. M1: gene cloning, sequencing, high-level expression and characterization. *Protein Expression and Purification* 51, 133-140 (2007).
36. Chu, X., He, H., Guo, C. & Sun, B. Identification of two novel esterases from a marine metagenomic library derived from South China Sea. *Appl Microbiol Biotechnol* 80, 615-25 (2008).
37. Ki-Hoon Oh et al. Characterization of a novel esterase isolated from intertidal flat metagenome and its tertiary alcohols synthesis. *Journal of Molecular Catalysis B: Enzymatic*, 67-73 (2012).
38. Lang Rao et al. A thermostable esterase from *Thermoanaerobacter tengcongensis* opening up a new family of bacterial lipolytic enzymes. *Biochimica et Biophysica Acta*, 1695-1702 (2011).
39. Nadia A. Soliman, Michael Knoll, Yasser R. Abdel-Fattah, Rolf D. Schmid & Lange, S. Molecular cloning and characterization of thermostable esterase and lipase from *Geobacillus thermoleovorans* YN isolated from desert soil in Egypt. *Process Biochemistry*, 1090-1100 (2007).
40. Özlem Faiz, Ahmet Colak, Nagihan Saglam, Sabriye Ç anakçi & Beldüz, A. O. Determination and Characterization of Thermostable Esterolytic Activity from a Novel Thermophilic Bacterium Anoxybacillus gonensis A4. *Journal of Biochemistry and Molecular Biology* 40, 588-594 (2007).
41. Luo, Z. H., et al. Purification and characterization of an intracellular esterase from a *Fusarium* species capable of degrading dimethyl terephthalate. *Process Biochemistry*, 687-693 (2012).
42. Juan Fu et al. Functional and structural studies of a novel cold-adapted esterase from an Arctic intertidal metagenomic library. *Applied Microbiology and Biotechnology* (2012).
43. Kubilay Metin, Z. Burcu Bakir Ateslier, Gamze Basbulbul & Biyik, H. H. Characterization of esterase activity in *Geobacillus* sp. HBB-4. *Journal of Basic Microbiology* 46, 400-409 (2006).
44. Jeong Ho Jeon et al. Identification of a new subfamily of salt-tolerant esterases from a metagenomic library of tidal flat sediment. *Applied Microbiology and Biotechnology*, 623-631 (2012).
45. Rhee J-K et. Al. (2005), New thermophilic and thermostable esterase with sequence homology to the hormone sensitive lipase family, cloned from a metagenomic library. *Appl Environ Microbiol* Vol. 71(2): pp. 817-825.
46. Yu, et al. (2010), Gene cloning and characterization of a novel thermophilic esterase from Fervidobacterium nodosum Rt17-B1, *Acta Biochim. Biophys. Sin.*, Vol. 42(4), pp. 288-295
47. Waters D M et al (2012), Cloning, Overexpression in *Escherichia coli*, and Characterization of a Thermostable Fungal Acetylxylan Esterase from *Talaromyces emersonii*, *Appl. Environ. Microbiol.* Vol. 78(10): pp. 3759-3762

48. Singh R K et al (2013), From protein engineering to immobilization: promising strategies for the upgrade of industrial enzymes. *Int. J. Mol. Sci.* Vol. 14: pp. 1232-1277.

49. Bornscheuer U T (2002) Microbial carboxyl esterases: classification, properties, and application in biocatalysis. *FEMS Microbiol. Rev.* Vol. 26: pp. 73-81

50. Cao H et al (2012) Biocatalytic synthesis of poly (δ-valerolactone) using a thermophilic esterase from *Archaeoglobus fulgidus* as catalyst. *Int. J. Mol. Sci.* Vol. 13: pp 12232-12241

The invention claimed is:

1. A chimeric or fusion polypeptide having esterase activity, wherein the polypeptide comprises an amino acid sequence that has at least 95% sequence identity to the amino acid sequence of SEQ ID NO: 2 and a heterologous amino acid sequence.

2. The chimeric or fusion polypeptide of claim 1, wherein the heterologous amino acid sequence is a polypeptide selected from the group consisting of galactosidase, glucuronidase, glutathione-S-transferase, horseradish peroxidase, and chloramphenicol acetyltransferase.

3. The chimeric or fusion polypeptide of claim 1, wherein the at least one heterologous amino acid sequence is a polypeptide selected from the group consisting of a fluorescent protein and luciferase.

4. The chimeric or fusion polypeptide of claim 1, further comprising a protein cleavage site.

5. A composition comprising the chimeric or fusion polypeptide of claim 1 and at least one secondary component comprising an ester linkage.

6. The polypeptide of claim 1, wherein the heterologous amino acid sequence is a purification tag.

7. The polypeptide of claim 6, wherein the purification tag is a histidine tag.

8. The polypeptide of claim 6, wherein the purification tag is a FLAG tag.

9. The polypeptide of claim 6, wherein the purification tag is an influenza hemagglutinin tag.

10. A composition comprising the polypeptide of claim 6 and at least one secondary component comprising an ester linkage.

11. A method for cleaving an ester linkage, the method comprising contacting a material comprising an ester linkage with the chimeric or fusion polypeptide of claim 1, to thereby cleave the ester linkage.

12. The method of claim 11, wherein the material comprising an ester linkage is selected from the group consisting of a dairy product, leather, cellulose, wood pulp, and paper.

13. A method for cleaving an ester linkage, the method comprising contacting a material comprising an ester linkage with the polypeptide of claim 6, to thereby cleave the ester linkage.

14. The method of claim 13, wherein the material comprising an ester linkage is selected from the group consisting of a dairy product, leather, cellulose, wood pulp, and paper.

15. A solid substrate comprising an isolated polypeptide having esterase activity, wherein the polypeptide comprises an amino acid sequence that has at least 95% sequence identity to the amino acid sequence of SEQ ID NO: 2, wherein the polypeptide is covalently attached to the solid substrate, and wherein the solid substrate is glass, plastic, a bead, or a silicon chip.

16. The solid substrate of claim 15, wherein the solid substrate is a glass slide, a glass tube, or a glass bead.

17. The solid substrate of claim 15, wherein the solid substrate is a plastic slide or a plastic tube.

18. The solid substrate of claim 15, wherein the solid substrate is a bead.

19. The solid substrate of claim 15, wherein the solid substrate is a silicon chip.

20. A composition comprising the solid substrate of claim 15 and at least one secondary component comprising an ester linkage.

21. A method for cleaving an ester linkage, the method comprising contacting a material comprising an ester linkage with the solid substrate of claim 15, to thereby cleave the ester linkage.

22. The method of claim 21, wherein the material comprising an ester linkage is selected from the group consisting of a dairy product, leather, cellulose, wood pulp, and paper.

* * * * *

UNITED STATES PATENT AND TRADEMARK OFFICE
CERTIFICATE OF CORRECTION

PATENT NO.         : 9,963,688 B2
APPLICATION NO.    : 14/779293
DATED              : May 8, 2018
INVENTOR(S)        : Hamza El Dorry et al.

It is certified that error appears in the above-identified patent and that said Letters Patent is hereby corrected as shown below:

On the Title Page

Item (71) Please remove "Hamza El Dorry" as the Applicant

Signed and Sealed this
Eighteenth Day of September, 2018

Andrei Iancu
*Director of the United States Patent and Trademark Office*